US006455026B1

(12) United States Patent
Mueller et al.

(10) Patent No.: US 6,455,026 B1
(45) Date of Patent: Sep. 24, 2002

(54) USE OF PROTEIN TYROSINE PHOSPHATASE ZETA AS A BIOMOLECULAR TARGET IN THE TREATMENT AND VISUALIZATION OF BRAIN TUMORS

(75) Inventors: Sabine Mueller, San Francisco, CA (US); Thorsten Melcher, San Francisco, CA (US); Daniel J. Chin, Foster City, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 09/816,703

(22) Filed: Mar. 23, 2001

(51) Int. Cl.$^7$ .................. A61K 51/00; A61M 36/14
(52) U.S. Cl. .................. 424/1.49; 424/1.11; 424/1.65; 424/9.1; 435/21
(58) Field of Search .................. 424/1.11, 1.49, 424/1.65, 1.69, 9.1, 9.3, 9.4, 9.5, 9.6; 435/6, 2, 195, 69.1, 698; 536/23.2

(56) References Cited

U.S. PATENT DOCUMENTS

| 5,558,852 A | 9/1996 | Bigner et al. ............... 424/1.49 |
| 5,604,094 A | 2/1997 | Schlessinger .................. 435/6 |
| 5,624,659 A | 4/1997 | Bigner et al. ............... 424/1.49 |
| 6,080,772 A | 6/2000 | Tang et al. .................. 514/370 |
| 6,150,532 A | 11/2000 | Mjalli et al. ................ 548/235 |
| 6,160,090 A | 12/2000 | Schlessinger et al. ........ 530/350 |

OTHER PUBLICATIONS

RPTPβ, Webpage information, BD Biosciences, 2001.
Levy, J.B., et al., "The Cloning of a Receptor–type Protein tyrosine Phosphatase Expressed in the Central Nervous System", *The Journal of Biological Chemistry*, 268:14; May 15, 1993, pp. 10573–10581.
Holland, S.J., et al., "Cell–contact–dependent signalling in axon growth and guidance: Eph receptor tyrosine kinases and receptor protein tyrosine phosphatase β", *Current Opinion in Neurobiology*, vol. 8, pp. 117–127, 1998.
Meng, K., et al., "Pleiotrophin signals increased tyrosine phosphorylation of β–catenin through inactivation of the intrinsic catalytic activity of the receptor–type protein tyrosine phosphatase β/ζ", *Proc. Natl. Acad. Sci USA*, 97:6, Mar. 14, 2000, pp. 2603–2608.
Milev, P., et al., "High Affinity Binding and Overlapping Localization of Neurocan and Phosphacan/Protein–tyrosine Phosphatase ζ/β with Tenascin–R, Amphoterin, and the Heparin–binging Growth–associated Molecule", *The Journal of Biological Chemistry*, 273:12; Mar. 20, 1998, pp. 6998–7005.
Maeda, N. et al., "A Receptor–like Protein–tyrosine Phosphatase PTPζ/RPTPβ Binds a Heparin–binding Growth Factor Midkine", *The Journal of Biological Chemistry*, 274:18, Apr. 30, 1999, pp. 12474–12479.

Goldmann, T., et al., "A receptor–type protein tyrosine phosphatase PTPζ is expressed in human cutaneous melanomas", *Folia Histochemica et Cytobiologica* 38:1, 2000, pp. 19–20.
Krueger, N.X., et al., "A human transmembrane protein–tyrosine–phosphatase, PTPζ, is expressed in brain and has an N–terminal receptor domain homologous to carbonic anhydrases", *Proc. Natl. Acad. Sci., USA*, vol. 89, Aug. 1992, pp. 7417–7421.
Milev, P., et al., "The Core Protein of the Chondroitin Sulfate Proteoglycan Phosphacan Is a High–affinity Ligand of Fibroblast Growth Factor–2 and Potentiates Its Mitogenic Activity", *The Journal of Biological Chemistry*, 273:34, Aug. 21, 1998, pp. 21439–21442.
Maeda, N. et al., "6B4 Proteoglycan/Phosphacan, an Extracellular Variant of Receptor–like Protein–tyrosine Phosphatase ζ/RPTBβ, Binds Pleiotrophin/Heparin–binding Growth–associated Molecule (HB–GAM)", *The Journal of Biological Chemistry*, 271:35, Aug. 30, 1996, pp. 21446–21452.
Xiao, Z.C., et al., "Isolation of a Tenascin–R Binding Protein from Mouse Brain Membranes", *The Journal of Biological Chemistry*, 272:51, Dec. 19, 1997, pp. 32092–32101.
Milev, P., et al., "The Fibrinogen–like Globe of Tenascin–C Mediates Its Interactions with Neurocan and Phosphacan/Protein–tyrosine Phosphatase–ζ/β", *The Journal of Biological Chemistry*, 272:24, Jun. 13, 1997, pp. 15501–15509.

*Primary Examiner*—Dameron L. Jones
(74) *Attorney, Agent, or Firm*—Pamela J. Sherwood; Bozicevic, Field & Francis LLP

(57) ABSTRACT

The present invention relates to the use of proteins which are differentially expressed in primary brain tumor tissues, as compared to normal brain tissues, as biomolecular targets for brain tumor treatment therapies. Specifically, the present invention relates to the use of immunotherapeutic and immunoimaging agents that specifically bind to human protein tyrosine phosphatase-zeta (PTPζ) for the treatment and visualization of brain tumors in patients. The present invention also provides compounds and pharmaceutically acceptable compositions for administration in the methods of the invention.

63 Claims, 1 Drawing Sheet

SEQUENCE LISTING

<160> NUMBER OF SEQ ID NOS: 2

<210> SEQ ID NO 1
<211> LENGTH: 7941
<212> TYPE: DNA
<213> ORGANISM: Homo sapiens
<220> FEATURE:
<221> NAME/KEY: CDS
<222> LOCATION: (148)..(7092)

<400> SEQUENCE: 1

```
cacacatacg cacgcacgat ctcacttcga tctatacact ggaggattaa aacaaacaaa       60
caaaaaaaac atttccttcg ctcccccctcc ctctccactc tgagaagcag aggagccgca      120
cggcgagggg ccgcagaccg tctggaa atg cga atc cta aag cgt ttc ctc gct      174
                               Met Arg Ile Leu Lys Arg Phe Leu Ala
                                 1               5 tgc att cag ctc ctc tgt gtt tgc cgc ctg gat tgg gct aat gga tac         222
Cys Ile Gln Leu Leu Cys Val Cys Arg Leu Asp Trp Ala Asn Gly Tyr
 10              15                  20                  25 tac aga caa cag aga aaa ctt gtt gaa gag att ggc tgg tcc tat aca         270
Tyr Arg Gln Gln Arg Lys Leu Val Glu Glu Ile Gly Trp Ser Tyr Thr
                 30                  35                  40 gga gca ctg aat caa aaa aat tgg gga aag aaa tat cca aca tgt aat         318
Gly Ala Leu Asn Gln Lys Asn Trp Gly Lys Lys Tyr Pro Thr Cys Asn
             45                  50                  55 agc cca aaa caa tct cct atc aat att gat gaa gat ctt aca caa gta         366
Ser Pro Lys Gln Ser Pro Ile Asn Ile Asp Glu Asp Leu Thr Gln Val
         60                  65                  70 aat gtg aat ctt aag aaa ctt aaa ttt cag ggt tgg gat aaa aca tca         414
Asn Val Asn Leu Lys Lys Leu Lys Phe Gln Gly Trp Asp Lys Thr Ser
     75                  80                  85
```

```
ttg gaa aac aca ttc att cat aac act ggg aaa aca gtg gaa att aat      462
Leu Glu Asn Thr Phe Ile His Asn Thr Gly Lys Thr Val Glu Ile Asn
 90              95                 100                 105 ctc act aat gac tac cgt gtc agc gga gga gtt tca gaa atg gtg ttt      510
Leu Thr Asn Asp Tyr Arg Val Ser Gly Gly Val Ser Glu Met Val Phe
                     110                 115                 120 aaa gca agc aag ata act ttt cac tgg gga aaa tgc aat atg tca tct      558
Lys Ala Ser Lys Ile Thr Phe His Trp Gly Lys Cys Asn Met Ser Ser
                 125                 130                 135 gat gga tca gag cat agt tta gaa gga caa aaa ttt cca ctt gag atg      606
Asp Gly Ser Glu His Ser Leu Glu Gly Gln Lys Phe Pro Leu Glu Met
             140                 145                 150 caa atc tac tgc ttt gat gcg gac cga ttt tca agt ttt gag gaa gca      654
Gln Ile Tyr Cys Phe Asp Ala Asp Arg Phe Ser Ser Phe Glu Glu Ala
         155                 160                 165 gtc aaa gga aaa ggg aag tta aga gct tta tcc att ttg ttt gag gtt      702
Val Lys Gly Lys Gly Lys Leu Arg Ala Leu Ser Ile Leu Phe Glu Val
170                 175                 180                 185 ggg aca gaa gaa aat ttg gat ttc aaa gcg att att gat gga gtc gaa      750
Gly Thr Glu Glu Asn Leu Asp Phe Lys Ala Ile Ile Asp Gly Val Glu
                     190                 195                 200 agt gtt agt cgt ttt ggg aag cag gct gct tta gat cca ttc ata ctg      798
Ser Val Ser Arg Phe Gly Lys Gln Ala Ala Leu Asp Pro Phe Ile Leu
                 205                 210                 215 ttg aac ctt ctg cca aac tca act gac aag tat tac att tac aat ggc      846
Leu Asn Leu Leu Pro Asn Ser Thr Asp Lys Tyr Tyr Ile Tyr Asn Gly
             220                 225                 230 tca ttg aca tct cct ccc tgc aca gac aca gtt gac tgg att gtt ttt      894
Ser Leu Thr Ser Pro Pro Cys Thr Asp Thr Val Asp Trp Ile Val Phe
         235                 240                 245 aaa gat aca gtt agc atc tct gaa agc cag ttg gct gtt ttt tgt gaa      942
Lys Asp Thr Val Ser Ile Ser Glu Ser Gln Leu Ala Val Phe Cys Glu
250                 255                 260                 265 gtt ctt aca atg caa caa tct ggt tat gtc atg ctg atg gac tac tta      990
Val Leu Thr Met Gln Gln Ser Gly Tyr Val Met Leu Met Asp Tyr Leu
                     270                 275                 280 caa aac aat ttt cga gag caa cag tac aag ttc tct aga cag gtg ttt     1038
Gln Asn Asn Phe Arg Glu Gln Gln Tyr Lys Phe Ser Arg Gln Val Phe
                 285                 290                 295 tcc tca tac act gga aag gaa gag att cat gaa gca gtt tgt agt tca     1086
Ser Ser Tyr Thr Gly Lys Glu Glu Ile His Glu Ala Val Cys Ser Ser
             300                 305                 310 gaa cca gaa aat gtt cag gct gac cca gag aat tat acc agc ctt ctt     1134
Glu Pro Glu Asn Val Gln Ala Asp Pro Glu Asn Tyr Thr Ser Leu Leu
         315                 320                 325 gtt aca tgg gaa aga cct cga gtc gtt tat gat acc atg att gag aag     1182
Val Thr Trp Glu Arg Pro Arg Val Val Tyr Asp Thr Met Ile Glu Lys
330                 335                 340                 345 ttt gca gtt ttg tac cag cag ttg gat gga gag gac caa acc aag cat     1230
Phe Ala Val Leu Tyr Gln Gln Leu Asp Gly Glu Asp Gln Thr Lys His
                     350                 355                 360 gaa ttt ttg aca gat ggc tat caa gac ttg ggt gct att ctc aat aat     1278
Glu Phe Leu Thr Asp Gly Tyr Gln Asp Leu Gly Ala Ile Leu Asn Asn
                 365                 370                 375 ttg cta ccc aat atg agt tat gtt ctt cag ata gta gcc ata tgc act     1326
Leu Leu Pro Asn Met Ser Tyr Val Leu Gln Ile Val Ala Ile Cys Thr
             380                 385                 390 aat ggc tta tat gga aaa tac agc gac caa ctg att gtc gac atg cct     1374
Asn Gly Leu Tyr Gly Lys Tyr Ser Asp Gln Leu Ile Val Asp Met Pro
```

```
                  395                   400                   405
act gat aat cct gaa ctt gat ctt ttc cct gaa tta att gga act gaa         1422
Thr Asp Asn Pro Glu Leu Asp Leu Phe Pro Glu Leu Ile Gly Thr Glu
410                 415                 420                 425 gaa ata atc aag gag gag gaa gag gga aaa gac att gaa gaa ggc gct         1470
Glu Ile Ile Lys Glu Glu Glu Glu Gly Lys Asp Ile Glu Glu Gly Ala
                430                 435                 440 att gtg aat cct ggt aga gac agt gct aca aac caa atc agg aaa aag         1518
Ile Val Asn Pro Gly Arg Asp Ser Ala Thr Asn Gln Ile Arg Lys Lys
            445                 450                 455 gaa ccc cag att tct acc aca aca cac tac aat cgc ata ggg acg aaa         1566
Glu Pro Gln Ile Ser Thr Thr Thr His Tyr Asn Arg Ile Gly Thr Lys
        460                 465                 470 tac aat gaa gcc aag act aac cga tcc cca aca aga gga agt gaa ttc         1614
Tyr Asn Glu Ala Lys Thr Asn Arg Ser Pro Thr Arg Gly Ser Glu Phe
475                 480                 485 tct gga aag ggt gat gtt ccc aat aca tct tta aat tcc act tcc caa         1662
Ser Gly Lys Gly Asp Val Pro Asn Thr Ser Leu Asn Ser Thr Ser Gln
490                 495                 500                 505 cca gtc act aaa tta gcc aca gaa aaa gat att tcc ttg act tct cag         1710
Pro Val Thr Lys Leu Ala Thr Glu Lys Asp Ile Ser Leu Thr Ser Gln
                510                 515                 520 act gtg act gaa ctg cca cct cac act gtg gaa ggt act tca gcc tct         1758
Thr Val Thr Glu Leu Pro Pro His Thr Val Glu Gly Thr Ser Ala Ser
            525                 530                 535 tta aat gat ggc tct aaa act gtt ctt aga tct cca cat atg aac ttg         1806
Leu Asn Asp Gly Ser Lys Thr Val Leu Arg Ser Pro His Met Asn Leu
        540                 545                 550 tcg ggg act gca gaa tcc tta aat aca gtt tct ata aca gaa tat gag         1854
Ser Gly Thr Ala Glu Ser Leu Asn Thr Val Ser Ile Thr Glu Tyr Glu
555                 560                 565 gag gag agt tta ttg acc agt ttc aag ctt gat act gga gct gaa gat         1902
Glu Glu Ser Leu Leu Thr Ser Phe Lys Leu Asp Thr Gly Ala Glu Asp
570                 575                 580                 585 tct tca ggc tcc agt ccc gca act tct gct atc cca ttc atc tct gag         1950
Ser Ser Gly Ser Ser Pro Ala Thr Ser Ala Ile Pro Phe Ile Ser Glu
                590                 595                 600 aac ata tcc caa ggg tat ata ttt tcc tcc gaa aac cca gag aca ata         1998
Asn Ile Ser Gln Gly Tyr Ile Phe Ser Ser Glu Asn Pro Glu Thr Ile
            605                 610                 615 aca tat gat gtc ctt ata cca gaa tct gct aga aat gct tcc gaa gat         2046
Thr Tyr Asp Val Leu Ile Pro Glu Ser Ala Arg Asn Ala Ser Glu Asp
        620                 625                 630 tca act tca tca ggt tca gaa gaa tca cta aag gat cct tct atg gag         2094
Ser Thr Ser Ser Gly Ser Glu Glu Ser Leu Lys Asp Pro Ser Met Glu
635                 640                 645 gga aat gtg tgg ttt cct agc tct aca gac ata aca gca cag ccc gat         2142
Gly Asn Val Trp Phe Pro Ser Ser Thr Asp Ile Thr Ala Gln Pro Asp
650                 655                 660                 665 gtt gga tca ggc aga gag agc ttt ctc cag act aat tac act gag ata         2190
Val Gly Ser Gly Arg Glu Ser Phe Leu Gln Thr Asn Tyr Thr Glu Ile
                670                 675                 680 cgt gtt gat gaa tct gag aag aca acc aag tcc ttt tct gca ggc cca         2238
Arg Val Asp Glu Ser Glu Lys Thr Thr Lys Ser Phe Ser Ala Gly Pro
            685                 690                 695 gtg atg tca cag ggt ccc tca gtt aca gat ctg gaa atg cca cat tat         2286
Val Met Ser Gln Gly Pro Ser Val Thr Asp Leu Glu Met Pro His Tyr
        700                 705                 710 tct acc ttt gcc tac ttc cca act gag gta aca cct cat gct ttt acc         2334
```

```
Ser Thr Phe Ala Tyr Phe Pro Thr Glu Val Thr Pro His Ala Phe Thr
    715                 720                 725 cca tcc tcc aga caa cag gat ttg gtc tcc acg gtc aac gtg gta tac      2382
Pro Ser Ser Arg Gln Gln Asp Leu Val Ser Thr Val Asn Val Val Tyr
730                 735                 740                 745 tcg cag aca acc caa ccg gta tac aat ggt gag aca cct ctt caa cct      2430
Ser Gln Thr Thr Gln Pro Val Tyr Asn Gly Glu Thr Pro Leu Gln Pro
                750                 755                 760 tcc tac agt agt gaa gtc ttt cct cta gtc acc cct ttg ttg ctt gac      2478
Ser Tyr Ser Ser Glu Val Phe Pro Leu Val Thr Pro Leu Leu Leu Asp
            765                 770                 775 aat cag atc ctc aac act acc cct gct gct tca agt agt gat tcg gcc      2526
Asn Gln Ile Leu Asn Thr Thr Pro Ala Ala Ser Ser Ser Asp Ser Ala
        780                 785                 790 ttg cat gct acg cct gta ttt ccc agt gtc gat gtg tca ttt gaa tcc      2574
Leu His Ala Thr Pro Val Phe Pro Ser Val Asp Val Ser Phe Glu Ser
    795                 800                 805 atc ctg tct tcc tat gat ggt gca cct ttg ctt cca ttt tcc tct gct      2622
Ile Leu Ser Ser Tyr Asp Gly Ala Pro Leu Leu Pro Phe Ser Ser Ala
810                 815                 820                 825 tcc ttc agt agt gaa ttg ttt cgc cat ctg cat aca gtt tct caa atc      2670
Ser Phe Ser Ser Glu Leu Phe Arg His Leu His Thr Val Ser Gln Ile
                830                 835                 840 ctt cca caa gtt act tca gct acc gag agt gat aag gtg ccc ttg cat      2718
Leu Pro Gln Val Thr Ser Ala Thr Glu Ser Asp Lys Val Pro Leu His
            845                 850                 855 gct tct ctg cca gtg gct ggg ggt gat ttg cta tta gag ccc agc ctt      2766
Ala Ser Leu Pro Val Ala Gly Gly Asp Leu Leu Leu Glu Pro Ser Leu
        860                 865                 870 gct cag tat tct gat gtg ctg tcc act act cat gct gct tca gag acg      2814
Ala Gln Tyr Ser Asp Val Leu Ser Thr Thr His Ala Ala Ser Glu Thr
    875                 880                 885 ctg gaa ttt ggt agt gaa tct ggt gtt ctt tat aaa acg ctt atg ttt      2862
Leu Glu Phe Gly Ser Glu Ser Gly Val Leu Tyr Lys Thr Leu Met Phe
890                 895                 900                 905 tct caa gtt gaa cca ccc agc agt gat gcc atg atg cat gca cgt tct      2910
Ser Gln Val Glu Pro Pro Ser Ser Asp Ala Met Met His Ala Arg Ser
                910                 915                 920 tca ggg cct gaa cct tct tat gcc ttg tct gat aat gag ggc tcc caa      2958
Ser Gly Pro Glu Pro Ser Tyr Ala Leu Ser Asp Asn Glu Gly Ser Gln
            925                 930                 935 cac atc ttc act gtt tct tac agt tct gca ata cct gtg cat gat tct      3006
His Ile Phe Thr Val Ser Tyr Ser Ser Ala Ile Pro Val His Asp Ser
        940                 945                 950 gtg ggt gta act tat cag ggt tcc tta ttt agc ggc cct agc cat ata      3054
Val Gly Val Thr Tyr Gln Gly Ser Leu Phe Ser Gly Pro Ser His Ile
    955                 960                 965 cca ata cct aag tct tcg tta ata acc cca act gca tca tta ctg cag      3102
Pro Ile Pro Lys Ser Ser Leu Ile Thr Pro Thr Ala Ser Leu Leu Gln
970                 975                 980                 985 cct act cat gcc ctc tct ggt gat ggg gaa tgg tct gga gcc tct  tct     3150
Pro Thr His Ala Leu Ser Gly Asp Gly Glu Trp Ser Gly Ala Ser  Ser
                990                 995                 1000 gat agt gaa ttt  ctt tta cct gac aca  gat ggg ctg aca gcc  ctt       3195
Asp Ser Glu Phe  Leu Leu Pro Asp Thr  Asp Gly Leu Thr Ala  Leu
                1005                1010                1015 aac att tct tca  cct gtt tct gta gct  gaa ttt aca tat aca  aca       3240
Asn Ile Ser Ser  Pro Val Ser Val Ala  Glu Phe Thr Tyr Thr  Thr
                1020                1025                1030
```

| | | | | | | | | | | | |
|---|---|---|---|---|---|---|---|---|---|---|---|
| tct | gtg | ttt | ggt | gat | gat | aat | aag | gcg | ctt | tct | aaa | agt | gaa | ata | 3285 |
| Ser | Val | Phe | Gly | Asp | Asp | Asn | Lys | Ala | Leu | Ser | Lys | Ser | Glu | Ile | |
| | | | 1035 | | | | 1040 | | | | 1045 | | | | |

```
tct gtg ttt ggt gat gat aat aag gcg ctt tct aaa agt gaa ata      3285
Ser Val Phe Gly Asp Asp Asn Lys Ala Leu Ser Lys Ser Glu Ile
            1035            1040             1045 ata tat gga aat gag act gaa ctg caa att cct tct ttc aat gag      3330
Ile Tyr Gly Asn Glu Thr Glu Leu Gln Ile Pro Ser Phe Asn Glu
            1050            1055             1060 atg gtt tac cct tct gaa agc aca gtc atg ccc aac atg tat gat      3375
Met Val Tyr Pro Ser Glu Ser Thr Val Met Pro Asn Met Tyr Asp
            1065            1070             1075 aat gta aat aag ttg aat gcg tct tta caa gaa acc tct gtt tcc      3420
Asn Val Asn Lys Leu Asn Ala Ser Leu Gln Glu Thr Ser Val Ser
            1080            1085             1090 att tct agc acc aag ggc atg ttt cca ggg tcc ctt gct cat acc      3465
Ile Ser Ser Thr Lys Gly Met Phe Pro Gly Ser Leu Ala His Thr
            1095            1100             1105 acc act aag gtt ttt gat cat gag att agt caa gtt cca gaa aat      3510
Thr Thr Lys Val Phe Asp His Glu Ile Ser Gln Val Pro Glu Asn
            1110            1115             1120 aac ttt tca gtt caa cct aca cat act gtc tct caa gca tct ggt      3555
Asn Phe Ser Val Gln Pro Thr His Thr Val Ser Gln Ala Ser Gly
            1125            1130             1135 gac act tcg ctt aaa cct gtg ctt agt gca aac tca gag cca gca      3600
Asp Thr Ser Leu Lys Pro Val Leu Ser Ala Asn Ser Glu Pro Ala
            1140            1145             1150 tcc tct gac cct gct tct agt gaa atg tta tct cct tca act cag      3645
Ser Ser Asp Pro Ala Ser Ser Glu Met Leu Ser Pro Ser Thr Gln
            1155            1160             1165 ctc tta ttt tat gag acc tca gct tct ttt agt act gaa gta ttg      3690
Leu Leu Phe Tyr Glu Thr Ser Ala Ser Phe Ser Thr Glu Val Leu
            1170            1175             1180 cta caa cct tcc ttt cag gct tct gat gtt gac acc ttg ctt aaa      3735
Leu Gln Pro Ser Phe Gln Ala Ser Asp Val Asp Thr Leu Leu Lys
            1185            1190             1195 act gtt ctt cca gct gtg ccc agt gat cca ata ttg gtt gaa acc      3780
Thr Val Leu Pro Ala Val Pro Ser Asp Pro Ile Leu Val Glu Thr
            1200            1205             1210 ccc aaa gtt gat aaa att agt tct aca atg ttg cat ctc att gta      3825
Pro Lys Val Asp Lys Ile Ser Ser Thr Met Leu His Leu Ile Val
            1215            1220             1225 tca aat tct gct tca agt gaa aac atg ctg cac tct aca tct gta      3870
Ser Asn Ser Ala Ser Ser Glu Asn Met Leu His Ser Thr Ser Val
            1230            1235             1240 cca gtt ttt gat gtg tcg cct act tct cat atg cac tct gct tca      3915
Pro Val Phe Asp Val Ser Pro Thr Ser His Met His Ser Ala Ser
            1245            1250             1255 ctt caa ggt ttg acc att tcc tat gca agt gag aaa tat gaa cca      3960
Leu Gln Gly Leu Thr Ile Ser Tyr Ala Ser Glu Lys Tyr Glu Pro
            1260            1265             1270 gtt ttg tta aaa agt gaa agt tcc cac caa gtg gta cct tct ttg      4005
Val Leu Leu Lys Ser Glu Ser Ser His Gln Val Val Pro Ser Leu
            1275            1280             1285 tac agt aat gat gag ttg ttc caa acg gcc aat ttg gag att aac      4050
Tyr Ser Asn Asp Glu Leu Phe Gln Thr Ala Asn Leu Glu Ile Asn
            1290            1295             1300 cag gcc cat ccc cca aaa gga agg cat gta ttt gct aca cct gtt      4095
Gln Ala His Pro Pro Lys Gly Arg His Val Phe Ala Thr Pro Val
            1305            1310             1315 tta tca att gat gaa cca tta aat aca cta ata aat aag ctt ata      4140
Leu Ser Ile Asp Glu Pro Leu Asn Thr Leu Ile Asn Lys Leu Ile
            1320            1325             1330
```

```
                                                     -continued cat tcc gat gaa att tta acc tcc acc aaa agt tct gtt act ggt        4185
His Ser Asp Glu Ile Leu Thr Ser Thr Lys Ser Ser Val Thr Gly
            1335                1340                1345 aag gta ttt gct ggt att cca aca gtt gct tct gat aca ttt gta        4230
Lys Val Phe Ala Gly Ile Pro Thr Val Ala Ser Asp Thr Phe Val
        1350                1355                1360 tct act gat cat tct gtt cct ata gga aat ggg cat gtt gcc att        4275
Ser Thr Asp His Ser Val Pro Ile Gly Asn Gly His Val Ala Ile
        1365                1370                1375 aca gct gtt tct ccc cac aga gat ggt tct gta acc tca aca aag        4320
Thr Ala Val Ser Pro His Arg Asp Gly Ser Val Thr Ser Thr Lys
        1380                1385                1390 ttg ctg ttt cct tct aag gca act tct gag ctg agt cat agt gcc        4365
Leu Leu Phe Pro Ser Lys Ala Thr Ser Glu Leu Ser His Ser Ala
        1395                1400                1405 aaa tct gat gcc ggt tta gtg ggt ggt ggt gaa gat ggt gac act        4410
Lys Ser Asp Ala Gly Leu Val Gly Gly Gly Glu Asp Gly Asp Thr
        1410                1415                1420 gat gat gat ggt gat gat gat gat gac aga gat agt gat ggc tta        4455
Asp Asp Asp Gly Asp Asp Asp Asp Asp Arg Asp Ser Asp Gly Leu
        1425                1430                1435 tcc att cat aag tgt atg tca tgc tca tcc tat aga gaa tca cag        4500
Ser Ile His Lys Cys Met Ser Cys Ser Ser Tyr Arg Glu Ser Gln
        1440                1445                1450 gaa aag gta atg aat gat tca gac acc cac gaa aac agt ctt atg        4545
Glu Lys Val Met Asn Asp Ser Asp Thr His Glu Asn Ser Leu Met
        1455                1460                1465 gat cag aat aat cca atc tca tac tca cta tct gag aat tct gaa        4590
Asp Gln Asn Asn Pro Ile Ser Tyr Ser Leu Ser Glu Asn Ser Glu
        1470                1475                1480 gaa gat aat aga gtc aca agt gta tcc tca gac agt caa act ggt        4635
Glu Asp Asn Arg Val Thr Ser Val Ser Ser Asp Ser Gln Thr Gly
        1485                1490                1495 atg gac aga agt cct ggt aaa tca cca tca gca aat ggg cta tcc        4680
Met Asp Arg Ser Pro Gly Lys Ser Pro Ser Ala Asn Gly Leu Ser
        1500                1505                1510 caa aag cac aat gat gga aaa gag gaa aat gac att cag act ggt        4725
Gln Lys His Asn Asp Gly Lys Glu Glu Asn Asp Ile Gln Thr Gly
        1515                1520                1525 agt gct ctg ctt cct ctc agc cct gaa tct aaa gca tgg gca gtt        4770
Ser Ala Leu Leu Pro Leu Ser Pro Glu Ser Lys Ala Trp Ala Val
        1530                1535                1540 ctg aca agt gat gaa gaa agt gga tca ggg caa ggt acc tca gat        4815
Leu Thr Ser Asp Glu Glu Ser Gly Ser Gly Gln Gly Thr Ser Asp
        1545                1550                1555 agc ctt aat gag aat gag act tcc aca gat ttc agt ttt gca gac        4860
Ser Leu Asn Glu Asn Glu Thr Ser Thr Asp Phe Ser Phe Ala Asp
        1560                1565                1570 act aat gaa aaa gat gct gat ggg atc ctg gca gca ggt gac tca        4905
Thr Asn Glu Lys Asp Ala Asp Gly Ile Leu Ala Ala Gly Asp Ser
        1575                1580                1585 gaa ata act cct gga ttc cca cag tcc cca aca tca tct gtt act        4950
Glu Ile Thr Pro Gly Phe Pro Gln Ser Pro Thr Ser Ser Val Thr
        1590                1595                1600 agc gag aac tca gaa gtg ttc cac gtt tca gag gca gag gcc agt        4995
Ser Glu Asn Ser Glu Val Phe His Val Ser Glu Ala Glu Ala Ser
        1605                1610                1615 aat agt agc cat gag tct cgt att ggt cta gct gag ggg ttg gaa        5040
Asn Ser Ser His Glu Ser Arg Ile Gly Leu Ala Glu Gly Leu Glu
```

|       |     |     |     |     |     |     |     |     |     |     |     |     |     |      |
|-------|-----|-----|-----|-----|-----|-----|-----|-----|-----|-----|-----|-----|-----|------|
|       |     |     | 1620|     |     |     | 1625|     |     |     | 1630|     |     |      |
| tcc   | gag | aag | aag | gca | gtt | ata | ccc | ctt | gtg | atc | gtg | tca | gcc | ctg  | 5085 |
| Ser   | Glu | Lys | Lys | Ala | Val | Ile | Pro | Leu | Val | Ile | Val | Ser | Ala | Leu  |
|       |     |     | 1635|     |     |     | 1640|     |     |     | 1645|     |     |      |
| act   | ttt | atc | tgt | cta | gtg | gtt | ctt | gtg | ggt | att | ctc | atc | tac | tgg  | 5130 |
| Thr   | Phe | Ile | Cys | Leu | Val | Val | Leu | Val | Gly | Ile | Leu | Ile | Tyr | Trp  |
|       |     |     | 1650|     |     |     | 1655|     |     |     | 1660|     |     |      |
| agg   | aaa | tgc | ttc | cag | act | gca | cac | ttt | tac | tta | gag | gac | agt | aca  | 5175 |
| Arg   | Lys | Cys | Phe | Gln | Thr | Ala | His | Phe | Tyr | Leu | Glu | Asp | Ser | Thr  |
|       |     |     | 1665|     |     |     | 1670|     |     |     | 1675|     |     |      |
| tcc   | cct | aga | gtt | ata | tcc | aca | cct | cca | aca | cct | atc | ttt | cca | att  | 5220 |
| Ser   | Pro | Arg | Val | Ile | Ser | Thr | Pro | Pro | Thr | Pro | Ile | Phe | Pro | Ile  |
|       |     |     | 1680|     |     |     | 1685|     |     |     | 1690|     |     |      |
| tca   | gat | gat | gtc | gga | gca | att | cca | ata | aag | cac | ttt | cca | aag | cat  | 5265 |
| Ser   | Asp | Asp | Val | Gly | Ala | Ile | Pro | Ile | Lys | His | Phe | Pro | Lys | His  |
|       |     |     | 1695|     |     |     | 1700|     |     |     | 1705|     |     |      |
| gtt   | gca | gat | tta | cat | gca | agt | agt | ggg | ttt | act | gaa | gaa | ttt | gag  | 5310 |
| Val   | Ala | Asp | Leu | His | Ala | Ser | Ser | Gly | Phe | Thr | Glu | Glu | Phe | Glu  |
|       |     |     | 1710|     |     |     | 1715|     |     |     | 1720|     |     |      |
| aca   | ctg | aaa | gag | ttt | tac | cag | gaa | gtg | cag | agc | tgt | act | gtt | gac  | 5355 |
| Thr   | Leu | Lys | Glu | Phe | Tyr | Gln | Glu | Val | Gln | Ser | Cys | Thr | Val | Asp  |
|       |     |     | 1725|     |     |     | 1730|     |     |     | 1735|     |     |      |
| tta   | ggt | att | aca | gca | gac | agc | tcc | aac | cac | cca | gac | aac | aag | cac  | 5400 |
| Leu   | Gly | Ile | Thr | Ala | Asp | Ser | Ser | Asn | His | Pro | Asp | Asn | Lys | His  |
|       |     |     | 1740|     |     |     | 1745|     |     |     | 1750|     |     |      |
| aag   | aat | cga | tac | ata | aat | atc | gtt | gcc | tat | gat | cat | agc | agg | gtt  | 5445 |
| Lys   | Asn | Arg | Tyr | Ile | Asn | Ile | Val | Ala | Tyr | Asp | His | Ser | Arg | Val  |
|       |     |     | 1755|     |     |     | 1760|     |     |     | 1765|     |     |      |
| aag   | cta | gca | cag | ctt | gct | gaa | aag | gat | ggc | aaa | ctg | act | gat | tat  | 5490 |
| Lys   | Leu | Ala | Gln | Leu | Ala | Glu | Lys | Asp | Gly | Lys | Leu | Thr | Asp | Tyr  |
|       |     |     | 1770|     |     |     | 1775|     |     |     | 1780|     |     |      |
| atc   | aat | gcc | aat | tat | gtt | gat | ggc | tac | aac | aga | cca | aaa | gct | tat  | 5535 |
| Ile   | Asn | Ala | Asn | Tyr | Val | Asp | Gly | Tyr | Asn | Arg | Pro | Lys | Ala | Tyr  |
|       |     |     | 1785|     |     |     | 1790|     |     |     | 1795|     |     |      |
| att   | gct | gcc | caa | ggc | cca | ctg | aaa | tcc | aca | gct | gaa | gat | ttc | tgg  | 5580 |
| Ile   | Ala | Ala | Gln | Gly | Pro | Leu | Lys | Ser | Thr | Ala | Glu | Asp | Phe | Trp  |
|       |     |     | 1800|     |     |     | 1805|     |     |     | 1810|     |     |      |
| aga   | atg | ata | tgg | gaa | cat | aat | gtg | gaa | gtt | att | gtc | atg | ata | aca  | 5625 |
| Arg   | Met | Ile | Trp | Glu | His | Asn | Val | Glu | Val | Ile | Val | Met | Ile | Thr  |
|       |     |     | 1815|     |     |     | 1820|     |     |     | 1825|     |     |      |
| aac   | ctc | gtg | gag | aaa | gga | agg | aga | aaa | tgt | gat | cag | tac | tgg | cct  | 5670 |
| Asn   | Leu | Val | Glu | Lys | Gly | Arg | Arg | Lys | Cys | Asp | Gln | Tyr | Trp | Pro  |
|       |     |     | 1830|     |     |     | 1835|     |     |     | 1840|     |     |      |
| gcc   | gat | ggg | agt | gag | gag | tac | ggg | aac | ttt | ctg | gtc | act | cag | aag  | 5715 |
| Ala   | Asp | Gly | Ser | Glu | Glu | Tyr | Gly | Asn | Phe | Leu | Val | Thr | Gln | Lys  |
|       |     |     | 1845|     |     |     | 1850|     |     |     | 1855|     |     |      |
| agt   | gtg | caa | gtg | ctt | gcc | tat | tat | act | gtg | agg | aat | ttt | act | cta  | 5760 |
| Ser   | Val | Gln | Val | Leu | Ala | Tyr | Tyr | Thr | Val | Arg | Asn | Phe | Thr | Leu  |
|       |     |     | 1860|     |     |     | 1865|     |     |     | 1870|     |     |      |
| aga   | aac | aca | aaa | ata | aaa | aag | ggc | tcc | cag | aaa | gga | aga | ccc | agt  | 5805 |
| Arg   | Asn | Thr | Lys | Ile | Lys | Lys | Gly | Ser | Gln | Lys | Gly | Arg | Pro | Ser  |
|       |     |     | 1875|     |     |     | 1880|     |     |     | 1885|     |     |      |
| gga   | cgt | gtg | gtc | aca | cag | tat | cac | tac | acg | cag | tgg | cct | gac | atg  | 5850 |
| Gly   | Arg | Val | Val | Thr | Gln | Tyr | His | Tyr | Thr | Gln | Trp | Pro | Asp | Met  |
|       |     |     | 1890|     |     |     | 1895|     |     |     | 1900|     |     |      |
| gga   | gta | cca | gag | tac | tcc | ctg | cca | gtg | ctg | acc | ttt | gtg | aga | aag  | 5895 |
| Gly   | Val | Pro | Glu | Tyr | Ser | Leu | Pro | Val | Leu | Thr | Phe | Val | Arg | Lys  |
|       |     |     | 1905|     |     |     | 1910|     |     |     | 1915|     |     |      |
| gca   | gcc | tat | gcc | aag | cgc | cat | gca | gtg | ggg | cct | gtt | gtc | gtc | cac  | 5940 |

```
                              -continued

Ala Ala Tyr Ala Lys Arg His Ala Val Gly Pro Val Val Val His
            1920            1925                1930 tgc agt gct gga gtt gga aga aca ggc aca tat att gtg cta gac      5985
Cys Ser Ala Gly Val Gly Arg Thr Gly Thr Tyr Ile Val Leu Asp
        1935                1940                1945 agt atg ttg cag cag att caa cac gaa gga act gtc aac ata ttt      6030
Ser Met Leu Gln Gln Ile Gln His Glu Gly Thr Val Asn Ile Phe
        1950                1955                1960 ggc ttc tta aaa cac atc cgt tca caa aga aat tat ttg gta caa      6075
Gly Phe Leu Lys His Ile Arg Ser Gln Arg Asn Tyr Leu Val Gln
        1965                1970                1975 act gag gag caa tat gtc ttc att cat gat aca ctg gtt gag gcc      6120
Thr Glu Glu Gln Tyr Val Phe Ile His Asp Thr Leu Val Glu Ala
        1980                1985                1990 ata ctt agt aaa gaa act gag gtg ctg gac agt cat att cat gcc      6165
Ile Leu Ser Lys Glu Thr Glu Val Leu Asp Ser His Ile His Ala
        1995                2000                2005 tat gtt aat gca ctc ctc att cct gga cca gca ggc aaa aca aag      6210
Tyr Val Asn Ala Leu Leu Ile Pro Gly Pro Ala Gly Lys Thr Lys
        2010                2015                2020 cta gag aaa caa ttc cag ctc ctg agc cag tca aat ata cag cag      6255
Leu Glu Lys Gln Phe Gln Leu Leu Ser Gln Ser Asn Ile Gln Gln
        2025                2030                2035 agt gac tat tct gca gcc cta aag caa tgc aac agg gaa aag aat      6300
Ser Asp Tyr Ser Ala Ala Leu Lys Gln Cys Asn Arg Glu Lys Asn
        2040                2045                2050 cga act tct tct atc atc cct gtg gaa aga tca agg gtt ggc att      6345
Arg Thr Ser Ser Ile Ile Pro Val Glu Arg Ser Arg Val Gly Ile
        2055                2060                2065 tca tcc ctg agt gga gaa ggc aca gac tac atc aat gcc tcc tat      6390
Ser Ser Leu Ser Gly Glu Gly Thr Asp Tyr Ile Asn Ala Ser Tyr
        2070                2075                2080 atc atg ggc tat tac cag agc aat gaa ttc atc att acc cag cac      6435
Ile Met Gly Tyr Tyr Gln Ser Asn Glu Phe Ile Ile Thr Gln His
        2085                2090                2095 cct ctc ctt cat acc atc aag gat ttc tgg agg atg ata tgg gac      6480
Pro Leu Leu His Thr Ile Lys Asp Phe Trp Arg Met Ile Trp Asp
        2100                2105                2110 cat aat gcc caa ctg gtg gtt atg att cct gat ggc caa aac atg      6525
His Asn Ala Gln Leu Val Val Met Ile Pro Asp Gly Gln Asn Met
        2115                2120                2125 gca gaa gat gaa ttt gtt tac tgg cca aat aaa gat gag cct ata      6570
Ala Glu Asp Glu Phe Val Tyr Trp Pro Asn Lys Asp Glu Pro Ile
        2130                2135                2140 aat tgt gag agc ttt aag gtc act ctc atg gct gaa gaa cac aaa      6615
Asn Cys Glu Ser Phe Lys Val Thr Leu Met Ala Glu Glu His Lys
        2145                2150                2155 tgt cta tct aat gag gaa aaa ctt ata att cag gac ttt atc tta      6660
Cys Leu Ser Asn Glu Glu Lys Leu Ile Ile Gln Asp Phe Ile Leu
        2160                2165                2170 gaa gct aca cag gat gat tat gta ctt gaa gtg agg cac ttt cag      6705
Glu Ala Thr Gln Asp Asp Tyr Val Leu Glu Val Arg His Phe Gln
        2175                2180                2185 tgt cct aaa tgg cca aat cca gat agc ccc att agt aaa act ttt      6750
Cys Pro Lys Trp Pro Asn Pro Asp Ser Pro Ile Ser Lys Thr Phe
        2190                2195                2200 gaa ctt ata agt gtt ata aaa gaa gaa gct gcc aat agg gat ggg      6795
Glu Leu Ile Ser Val Ile Lys Glu Glu Ala Ala Asn Arg Asp Gly
        2205                2210                2215
```

```
cct atg att gtt cat gat gag cat gga gga gtg acg gca gga act      6840
Pro Met Ile Val His Asp Glu His Gly Gly Val Thr Ala Gly Thr
        2220                2225                2230 ttc tgt gct ctg aca acc ctt atg cac caa cta gaa aaa gaa aat      6885
Phe Cys Ala Leu Thr Thr Leu Met His Gln Leu Glu Lys Glu Asn
        2235                2240                2245 tcc gtg gat gtt tac cag gta gcc aag atg atc aat ctg atg agg      6930
Ser Val Asp Val Tyr Gln Val Ala Lys Met Ile Asn Leu Met Arg
        2250                2255                2260 cca gga gtc ttt gct gac att gag cag tat cag ttt ctc tac aaa      6975
Pro Gly Val Phe Ala Asp Ile Glu Gln Tyr Gln Phe Leu Tyr Lys
        2265                2270                2275 gtg atc ctc agc ctt gtg agc aca agg cag gaa gag aat cca tcc      7020
Val Ile Leu Ser Leu Val Ser Thr Arg Gln Glu Glu Asn Pro Ser
        2280                2285                2290 acc tct ctg gac agt aat ggt gca gca ttg cct gat gga aat ata      7065
Thr Ser Leu Asp Ser Asn Gly Ala Ala Leu Pro Asp Gly Asn Ile
        2295                2300                2305 gct gag agc tta gag tct tta gtt taa cacagaaagg ggtgggggga        7112
Ala Glu Ser Leu Glu Ser Leu Val
        2310 ctcacatctg agcattgttt tcctcttcct aaaattaggc aggaaaatca gtctagttct    7172
gttatctgtt gatttcccat cacctgacag taactttcat gacataggat tctgccgcca    7232
aatttatatc attaacaatg tgtgcctttt tgcaagactt gtaatttact tattatgttt    7292
gaactaaaat gattgaattt tacagtattt ctaagaatgg aattgtggta tttttttctg    7352
tattgatttt aacagaaaat ttcaattat agaggttagg aattccaaac tacagaaaat    7412
gtttgttttt agtgtcaaat ttttagctgt atttgtagca attatcaggt ttgctagaaa    7472
tataacttttt aatacagtag cctgtaaata aaacactctt ccatatgata ttcaacattt    7532
tacaactgca gtattcacct aaagtagaaa taatctgtta cttattgtaa atactgccct    7592
agtgtctcca tggaccaaat ttatatttat aattgtagat ttttatattt tactactgag    7652
tcaagttttc tagttctgtg taattgttta gtttaatgac gtagttcatt agctggtctt    7712
actctaccag ttttctgaca ttgtattgtg ttacctaagt cattaacttt gtttcagcat    7772
gtaattttaa cttttgtgga aaatagaaat accttcattt tgaaagaagt ttttatgaga    7832
ataacacctt accaaacatt gttcaaatgg tttttatcca aggaattgca aaaataaata    7892
taaatattgc cattaaaaaa aaaaaaaaaa aaaaaaaaa aaaaaaaa              7941

<210> SEQ ID NO 2
<211> LENGTH: 2314
<212> TYPE: PRT
<213> ORGANISM: Homo sapiens
<220> FEATURE:
<221> NAME/KEY: Reference
<222> LOCATION: (1)..(2314)
<223> OTHER INFORMATION: Krueger, N.X. and Saito, H.: A human
      transmembrane protein-tyrosi ne-phosphatase, PTP zeta, is
      expressed in brain and has an N-term inal receptor domain
      homologous to carbonic anhydrases; Proc. Nat l. Acad. Sci. USA 89
      (16), 7417-7421 (1992
<221> NAME/KEY: Reference
<222> LOCATION: (1)..(2314)
<223> OTHER INFORMATION: Levy, J.B., et al.; The cloning of a
      receptor-type protein tyrosi ne phosphatase expressed in the
      central nervous system; J. Biol. Chem. 268 (14), 10573-10581 (1993
<221> NAME/KEY: SIGNAL
<222> LOCATION: (1)..(24)
<223> OTHER INFORMATION: By similarity
<221> NAME/KEY: DOMAIN
<222> LOCATION: (25)..(1635)
```

```
<223> OTHER INFORMATION: Extracellular (potential)
<221> NAME/KEY: misc_feature
<222> LOCATION: (25)..(2314)
<223> OTHER INFORMATION: Mature chain; protein-tyrosine phosphatase zeta
<221> NAME/KEY: DOMAIN
<222> LOCATION: (34)..(302)
<223> OTHER INFORMATION: Carbonic-anhydrase like
<221> NAME/KEY: SITE
<222> LOCATION: (105)..(105)
<223> OTHER INFORMATION: Glycosylation; N-linked (GLCNAC...) (potential)
<221> NAME/KEY: SITE
<222> LOCATION: (134)..(134)
<223> OTHER INFORMATION: Glycosylation; N-linked (GLCNAC...) (potential)
<221> NAME/KEY: SITE
<222> LOCATION: (223)..(223)
<223> OTHER INFORMATION: Glycosylation; N-linked (GLCNAC...) (potential)
<221> NAME/KEY: SITE
<222> LOCATION: (232)..(232)
<223> OTHER INFORMATION: Glycosylation; N-linked (GLCNAC...) (potential)
<221> NAME/KEY: DOMAIN
<222> LOCATION: (312)..(406)
<223> OTHER INFORMATION: Fibronectin Type-III
<221> NAME/KEY: SITE
<222> LOCATION: (324)..(324)
<223> OTHER INFORMATION: Glycosylation; N-linked (GLCNAC...) (potential)
<221> NAME/KEY: SITE
<222> LOCATION: (381)..(381)
<223> OTHER INFORMATION: Glycosylation; N-linked (GLCNAC...) (potential)
<221> NAME/KEY: SITE
<222> LOCATION: (497)..(497)
<223> OTHER INFORMATION: Glycosylation; N-linked (GLCNAC...) (potential)
<221> NAME/KEY: SITE
<222> LOCATION: (501)..(501)
<223> OTHER INFORMATION: Glycosylation; N-linked (GLCNAC...) (potential)
<221> NAME/KEY: SITE
<222> LOCATION: (552)..(552)
<223> OTHER INFORMATION: Glycosylation; N-linked (GLCNAC...) (potential)
<221> NAME/KEY: BINDING
<222> LOCATION: (587)..(587)
<223> OTHER INFORMATION: Chondroitin sulfate (potential)
<221> NAME/KEY: SITE
<222> LOCATION: (602)..(602)
<223> OTHER INFORMATION: Glycosylation; N-linked (GLCNAC...) (potential)
<221> NAME/KEY: SITE
<222> LOCATION: (629)..(629)
<223> OTHER INFORMATION: Glycosylation; N-linked (GLCNAC...) (potential)
<221> NAME/KEY: BINDING
<222> LOCATION: (637)..(637)
<223> OTHER INFORMATION: Chondroitin sulfate (potential)
<221> NAME/KEY: SITE
<222> LOCATION: (677)..(677)
<223> OTHER INFORMATION: Glycosylation; N-linked (GLCNAC...) (potential)
<221> NAME/KEY: VARSPLIC
<222> LOCATION: (755)..(1614)
<223> OTHER INFORMATION: Splicing variant; missing (in short isoform)
<221> NAME/KEY: BINDING
<222> LOCATION: (997)..(997)
<223> OTHER INFORMATION: Chondroitin sulfate (potential)
<221> NAME/KEY: SITE
<222> LOCATION: (1017)..(1017)
<223> OTHER INFORMATION: Glycosylation; N-linked (GLCNAC...) (potential)
<221> NAME/KEY: SITE
<222> LOCATION: (1050)..(1050)
<223> OTHER INFORMATION: Glycosylation; N-linked (GLCNAC...) (potential)
<221> NAME/KEY: SITE
<222> LOCATION: (1082)..(1082)
<223> OTHER INFORMATION: Glycosylation; N-linked (GLCNAC...) (potential)
<221> NAME/KEY: SITE
<222> LOCATION: (1122)..(1122)
<223> OTHER INFORMATION: Glycosylation; N-linked (GLCNAC...) (potential)
<221> NAME/KEY: SITE
<222> LOCATION: (1456)..(1456)
<223> OTHER INFORMATION: Glycosylation; N-linked (GLCNAC...) (potential)
<221> NAME/KEY: BINDING
<222> LOCATION: (1548)..(1548)
<223> OTHER INFORMATION: Chondroitin sulfate (potential)
<221> NAME/KEY: BINDING
<222> LOCATION: (1550)..(1550)
<223> OTHER INFORMATION: Chondroitin sulfate (potential)
```

```
<221> NAME/KEY: SITE
<222> LOCATION: (1561)..(1561)
<223> OTHER INFORMATION: Glycosylation; N-linked (GLCNAC ...)
      (potential)
<221> NAME/KEY: SITE
<222> LOCATION: (1617)..(1617)
<223> OTHER INFORMATION: Glycosylation; N-linked (GLCNAC ...)
      (potential)
<221> NAME/KEY: TRANSMEM
<222> LOCATION: (1636)..(1661)
<223> OTHER INFORMATION: Transmembrane region; potential
<221> NAME/KEY: DOMAIN
<222> LOCATION: (1662)..(2314)
<223> OTHER INFORMATION: Cytoplasmic (potential)
<221> NAME/KEY: CONFLICT
<222> LOCATION: (1722)..(1728)
<223> OTHER INFORMATION: Missing (in ref. 2)
<221> NAME/KEY: DOMAIN
<222> LOCATION: (1744)..(1997)
<223> OTHER INFORMATION: Protein-tyrosine phosphatase
<221> NAME/KEY: ACT_SITE
<222> LOCATION: (1932)..(1932)
<223> OTHER INFORMATION: Active site; by similarity
<221> NAME/KEY: DOMAIN
<222> LOCATION: (1998)..(2314)
<223> OTHER INFORMATION: Protein-tyrosine phosphatase
<221> NAME/KEY: misc_feature
<222> LOCATION: (2222)..(2222)
<223> OTHER INFORMATION: Ancestral active site

<400> SEQUENCE: 2

Met Arg Ile Leu Lys Arg Phe Leu Ala Cys Ile Gln Leu Leu Cys Val
1               5                   10                  15

Cys Arg Leu Asp Trp Ala Asn Gly Tyr Tyr Arg Gln Gln Arg Lys Leu
            20                  25                  30

Val Glu Glu Ile Gly Trp Ser Tyr Thr Gly Ala Leu Asn Gln Lys Asn
        35                  40                  45

Trp Gly Lys Lys Tyr Pro Thr Cys Asn Ser Pro Lys Gln Ser Pro Ile
    50                  55                  60

Asn Ile Asp Glu Asp Leu Thr Gln Val Asn Val Asn Leu Lys Lys Leu
65                  70                  75                  80

Lys Phe Gln Gly Trp Asp Lys Thr Ser Leu Glu Asn Thr Phe Ile His
                85                  90                  95

Asn Thr Gly Lys Thr Val Glu Ile Asn Leu Thr Asn Asp Tyr Arg Val
            100                 105                 110

Ser Gly Gly Val Ser Glu Met Val Phe Lys Ala Ser Lys Ile Thr Phe
        115                 120                 125

His Trp Gly Lys Cys Asn Met Ser Ser Asp Gly Ser Glu His Ser Leu
    130                 135                 140

Glu Gly Gln Lys Phe Pro Leu Glu Met Gln Ile Tyr Cys Phe Asp Ala
145                 150                 155                 160

Asp Arg Phe Ser Ser Phe Glu Glu Ala Val Lys Gly Lys Gly Lys Leu
                165                 170                 175

Arg Ala Leu Ser Ile Leu Phe Glu Val Gly Thr Glu Glu Asn Leu Asp
            180                 185                 190

Phe Lys Ala Ile Ile Asp Gly Val Glu Ser Val Ser Arg Phe Gly Lys
        195                 200                 205

Gln Ala Ala Leu Asp Pro Phe Ile Leu Leu Asn Leu Leu Pro Asn Ser
    210                 215                 220

Thr Asp Lys Tyr Tyr Ile Tyr Asn Gly Ser Leu Thr Ser Pro Pro Cys
225                 230                 235                 240

Thr Asp Thr Val Asp Trp Ile Val Phe Lys Asp Thr Val Ser Ile Ser
                245                 250                 255
```

-continued

```
Glu Ser Gln Leu Ala Val Phe Cys Glu Val Leu Thr Met Gln Gln Ser
            260                 265                 270
Gly Tyr Val Met Leu Met Asp Tyr Leu Gln Asn Asn Phe Arg Glu Gln
            275                 280             285
Gln Tyr Lys Phe Ser Arg Gln Val Phe Ser Ser Tyr Thr Gly Lys Glu
            290                 295                 300
Glu Ile His Glu Ala Val Cys Ser Ser Glu Pro Glu Asn Val Gln Ala
305                     310                 315                 320
Asp Pro Glu Asn Tyr Thr Ser Leu Leu Val Thr Trp Glu Arg Pro Arg
                325                 330                 335
Val Val Tyr Asp Thr Met Ile Glu Lys Phe Ala Val Leu Tyr Gln Gln
            340                 345                 350
Leu Asp Gly Glu Asp Gln Thr Lys His Glu Phe Leu Thr Asp Gly Tyr
            355                 360                 365
Gln Asp Leu Gly Ala Ile Leu Asn Asn Leu Leu Pro Asn Met Ser Tyr
            370                 375                 380
Val Leu Gln Ile Val Ala Ile Cys Thr Asn Gly Leu Tyr Gly Lys Tyr
385                 390                 395                 400
Ser Asp Gln Leu Ile Val Asp Met Pro Thr Asp Asn Pro Glu Leu Asp
                405                 410                 415
Leu Phe Pro Glu Leu Ile Gly Thr Glu Glu Ile Ile Lys Glu Glu Glu
                420                 425                 430
Glu Gly Lys Asp Ile Glu Glu Gly Ala Ile Val Asn Pro Gly Arg Asp
            435                 440                 445
Ser Ala Thr Asn Gln Ile Arg Lys Lys Glu Pro Gln Ile Ser Thr Thr
450                 455                 460
Thr His Tyr Asn Arg Ile Gly Thr Lys Tyr Asn Glu Ala Lys Thr Asn
465                 470                 475                 480
Arg Ser Pro Thr Arg Gly Ser Glu Phe Ser Gly Lys Gly Asp Val Pro
                485                 490                 495
Asn Thr Ser Leu Asn Ser Thr Ser Gln Pro Val Thr Lys Leu Ala Thr
                500                 505                 510
Glu Lys Asp Ile Ser Leu Thr Ser Gln Thr Val Thr Glu Leu Pro Pro
            515                 520                 525
His Thr Val Glu Gly Thr Ser Ala Ser Leu Asn Asp Gly Ser Lys Thr
530                 535                 540
Val Leu Arg Ser Pro His Met Asn Leu Ser Gly Thr Ala Glu Ser Leu
545                 550                 555                 560
Asn Thr Val Ser Ile Thr Glu Tyr Glu Glu Ser Leu Leu Thr Ser
                565                 570                 575
Phe Lys Leu Asp Thr Gly Ala Glu Asp Ser Ser Gly Ser Ser Pro Ala
            580                 585                 590
Thr Ser Ala Ile Pro Phe Ile Ser Glu Asn Ile Ser Gln Gly Tyr Ile
            595                 600                 605
Phe Ser Ser Glu Asn Pro Glu Thr Ile Thr Tyr Asp Val Leu Ile Pro
            610                 615                 620
Glu Ser Ala Arg Asn Ala Ser Glu Asp Ser Thr Ser Ser Gly Ser Glu
625                 630                 635                 640
Glu Ser Leu Lys Asp Pro Ser Met Glu Gly Asn Val Trp Phe Pro Ser
                645                 650                 655
Ser Thr Asp Ile Thr Ala Gln Pro Asp Val Gly Ser Gly Arg Glu Ser
                660                 665                 670
```

```
Phe Leu Gln Thr Asn Tyr Thr Glu Ile Arg Val Asp Glu Ser Glu Lys
            675                 680                 685

Thr Thr Lys Ser Phe Ser Ala Gly Pro Val Met Ser Gln Gly Pro Ser
        690                 695                 700

Val Thr Asp Leu Glu Met Pro His Tyr Ser Thr Phe Ala Tyr Phe Pro
705                 710                 715                 720

Thr Glu Val Thr Pro His Ala Phe Thr Pro Ser Ser Arg Gln Gln Asp
                725                 730                 735

Leu Val Ser Thr Val Asn Val Val Tyr Ser Gln Thr Thr Gln Pro Val
            740                 745                 750

Tyr Asn Gly Glu Thr Pro Leu Gln Pro Ser Tyr Ser Ser Glu Val Phe
            755                 760                 765

Pro Leu Val Thr Pro Leu Leu Leu Asp Asn Gln Ile Leu Asn Thr Thr
770                 775                 780

Pro Ala Ala Ser Ser Asp Ser Ala Leu His Ala Thr Pro Val Phe
785                 790                 795                 800

Pro Ser Val Asp Val Ser Phe Glu Ser Ile Leu Ser Ser Tyr Asp Gly
                805                 810                 815

Ala Pro Leu Leu Pro Phe Ser Ser Ala Ser Phe Ser Ser Glu Leu Phe
            820                 825                 830

Arg His Leu His Thr Val Ser Gln Ile Leu Pro Gln Val Thr Ser Ala
            835                 840                 845

Thr Glu Ser Asp Lys Val Pro Leu His Ala Ser Leu Pro Val Ala Gly
    850                 855                 860

Gly Asp Leu Leu Leu Glu Pro Ser Leu Ala Gln Tyr Ser Asp Val Leu
865                 870                 875                 880

Ser Thr Thr His Ala Ala Ser Glu Thr Leu Glu Phe Gly Ser Glu Ser
                885                 890                 895

Gly Val Leu Tyr Lys Thr Leu Met Phe Ser Gln Val Glu Pro Pro Ser
            900                 905                 910

Ser Asp Ala Met Met His Ala Arg Ser Ser Gly Pro Glu Pro Ser Tyr
            915                 920                 925

Ala Leu Ser Asp Asn Glu Gly Ser Gln His Ile Phe Thr Val Ser Tyr
    930                 935                 940

Ser Ser Ala Ile Pro Val His Asp Ser Val Gly Val Thr Tyr Gln Gly
945                 950                 955                 960

Ser Leu Phe Ser Gly Pro Ser His Ile Pro Ile Pro Lys Ser Ser Leu
            965                 970                 975

Ile Thr Pro Thr Ala Ser Leu Leu Gln Pro Thr His Ala Leu Ser Gly
            980                 985                 990

Asp Gly Glu Trp Ser Gly Ala Ser  Ser Asp Ser Glu Phe Leu Leu Pro
            995                1000               1005

Asp Thr Asp Gly Leu Thr Ala  Leu Asn Ile Ser Ser  Pro Val Ser
    1010                1015               1020

Val Ala Glu Phe Thr Tyr Thr  Thr Ser Val Phe Gly  Asp Asp Asn
    1025                1030               1035

Lys Ala Leu Ser Lys Ser Glu  Ile Ile Tyr Gly Asn  Glu Thr Glu
    1040                1045               1050

Leu Gln Ile Pro Ser Phe Asn  Glu Met Val Tyr Pro  Ser Glu Ser
    1055                1060               1065

Thr Val Met Pro Asn Met Tyr  Asp Asn Val Asn Lys  Leu Asn Ala
    1070                1075               1080

Ser Leu Gln Glu Thr Ser Val  Ser Ile Ser Ser Thr  Lys Gly Met
```

-continued

```
             1085                1090                1095

Phe   Pro   Gly   Ser   Leu   Ala   His   Thr   Thr   Thr   Lys   Val   Phe   Asp   His
             1100                1105                1110

Glu   Ile   Ser   Gln   Val   Pro   Glu   Asn   Asn   Phe   Ser   Val   Gln   Pro   Thr
             1115                1120                1125

His   Thr   Val   Ser   Gln   Ala   Ser   Gly   Asp   Thr   Ser   Leu   Lys   Pro   Val
             1130                1135                1140

Leu   Ser   Ala   Asn   Ser   Glu   Pro   Ala   Ser   Ser   Asp   Pro   Ala   Ser   Ser
             1145                1150                1155

Glu   Met   Leu   Ser   Pro   Ser   Thr   Gln   Leu   Leu   Phe   Tyr   Glu   Thr   Ser
             1160                1165                1170

Ala   Ser   Phe   Ser   Thr   Glu   Val   Leu   Leu   Gln   Pro   Ser   Phe   Gln   Ala
             1175                1180                1185

Ser   Asp   Val   Asp   Thr   Leu   Leu   Lys   Thr   Val   Leu   Pro   Ala   Val   Pro
             1190                1195                1200

Ser   Asp   Pro   Ile   Leu   Val   Glu   Thr   Pro   Lys   Val   Asp   Lys   Ile   Ser
             1205                1210                1215

Ser   Thr   Met   Leu   His   Leu   Ile   Val   Ser   Asn   Ser   Ala   Ser   Ser   Glu
             1220                1225                1230

Asn   Met   Leu   His   Ser   Thr   Ser   Val   Pro   Val   Phe   Asp   Val   Ser   Pro
             1235                1240                1245

Thr   Ser   His   Met   His   Ser   Ala   Ser   Leu   Gln   Gly   Leu   Thr   Ile   Ser
             1250                1255                1260

Tyr   Ala   Ser   Glu   Lys   Tyr   Glu   Pro   Val   Leu   Leu   Lys   Ser   Glu   Ser
             1265                1270                1275

Ser   His   Gln   Val   Val   Pro   Ser   Leu   Tyr   Ser   Asn   Asp   Glu   Leu   Phe
             1280                1285                1290

Gln   Thr   Ala   Asn   Leu   Glu   Ile   Asn   Gln   Ala   His   Pro   Pro   Lys   Gly
             1295                1300                1305

Arg   His   Val   Phe   Ala   Thr   Pro   Val   Leu   Ser   Ile   Asp   Glu   Pro   Leu
             1310                1315                1320

Asn   Thr   Leu   Ile   Asn   Lys   Leu   Ile   His   Ser   Asp   Glu   Ile   Leu   Thr
             1325                1330                1335

Ser   Thr   Lys   Ser   Ser   Val   Thr   Gly   Lys   Val   Phe   Ala   Gly   Ile   Pro
             1340                1345                1350

Thr   Val   Ala   Ser   Asp   Thr   Phe   Val   Ser   Thr   Asp   His   Ser   Val   Pro
             1355                1360                1365

Ile   Gly   Asn   Gly   His   Val   Ala   Ile   Thr   Ala   Val   Ser   Pro   His   Arg
             1370                1375                1380

Asp   Gly   Ser   Val   Thr   Ser   Thr   Lys   Leu   Leu   Phe   Pro   Ser   Lys   Ala
             1385                1390                1395

Thr   Ser   Glu   Leu   Ser   His   Ser   Ala   Lys   Ser   Asp   Ala   Gly   Leu   Val
             1400                1405                1410

Gly   Gly   Gly   Glu   Asp   Gly   Asp   Thr   Asp   Asp   Gly   Asp   Asp   Asp
             1415                1420                1425

Asp   Asp   Arg   Asp   Ser   Asp   Gly   Leu   Ser   Ile   His   Lys   Cys   Met   Ser
             1430                1435                1440

Cys   Ser   Ser   Tyr   Arg   Glu   Ser   Gln   Glu   Lys   Val   Met   Asn   Asp   Ser
             1445                1450                1455

Asp   Thr   His   Glu   Asn   Ser   Leu   Met   Asp   Gln   Asn   Asn   Pro   Ile   Ser
             1460                1465                1470

Tyr   Ser   Leu   Ser   Glu   Asn   Ser   Glu   Glu   Asp   Asn   Arg   Val   Thr   Ser
             1475                1480                1485
```

-continued

```
Val Ser Ser Asp Ser Gln Thr Gly Met Asp Arg Ser Pro Gly Lys
    1490                1495                1500
Ser Pro Ser Ala Asn Gly Leu Ser Gln Lys His Asn Asp Gly Lys
    1505                1510                1515
Glu Glu Asn Asp Ile Gln Thr Gly Ser Ala Leu Leu Pro Leu Ser
    1520                1525                1530
Pro Glu Ser Lys Ala Trp Ala Val Leu Thr Ser Asp Glu Glu Ser
    1535                1540                1545
Gly Ser Gly Gln Gly Thr Ser Asp Ser Leu Asn Glu Asn Glu Thr
    1550                1555                1560
Ser Thr Asp Phe Ser Phe Ala Asp Thr Asn Glu Lys Asp Ala Asp
    1565                1570                1575
Gly Ile Leu Ala Ala Gly Asp Ser Glu Ile Thr Pro Gly Phe Pro
    1580                1585                1590
Gln Ser Pro Thr Ser Ser Val Thr Ser Glu Asn Ser Glu Val Phe
    1595                1600                1605
His Val Ser Glu Ala Glu Ala Ser Asn Ser Ser His Glu Ser Arg
    1610                1615                1620
Ile Gly Leu Ala Glu Gly Leu Glu Ser Glu Lys Lys Ala Val Ile
    1625                1630                1635
Pro Leu Val Ile Val Ser Ala Leu Thr Phe Ile Cys Leu Val Val
    1640                1645                1650
Leu Val Gly Ile Leu Ile Tyr Trp Arg Lys Cys Phe Gln Thr Ala
    1655                1660                1665
His Phe Tyr Leu Glu Asp Ser Thr Ser Pro Arg Val Ile Ser Thr
    1670                1675                1680
Pro Pro Thr Pro Ile Phe Pro Ile Ser Asp Asp Val Gly Ala Ile
    1685                1690                1695
Pro Ile Lys His Phe Pro Lys His Val Ala Asp Leu His Ala Ser
    1700                1705                1710
Ser Gly Phe Thr Glu Glu Phe Glu Thr Leu Lys Glu Phe Tyr Gln
    1715                1720                1725
Glu Val Gln Ser Cys Thr Val Asp Leu Gly Ile Thr Ala Asp Ser
    1730                1735                1740
Ser Asn His Pro Asp Asn Lys His Lys Asn Arg Tyr Ile Asn Ile
    1745                1750                1755
Val Ala Tyr Asp His Ser Arg Val Lys Leu Ala Gln Leu Ala Glu
    1760                1765                1770
Lys Asp Gly Lys Leu Thr Asp Tyr Ile Asn Ala Asn Tyr Val Asp
    1775                1780                1785
Gly Tyr Asn Arg Pro Lys Ala Tyr Ile Ala Ala Gln Gly Pro Leu
    1790                1795                1800
Lys Ser Thr Ala Glu Asp Phe Trp Arg Met Ile Trp Glu His Asn
    1805                1810                1815
Val Glu Val Ile Val Met Ile Thr Asn Leu Val Glu Lys Gly Arg
    1820                1825                1830
Arg Lys Cys Asp Gln Tyr Trp Pro Ala Asp Gly Ser Glu Glu Tyr
    1835                1840                1845
Gly Asn Phe Leu Val Thr Gln Lys Ser Val Gln Val Leu Ala Tyr
    1850                1855                1860
Tyr Thr Val Arg Asn Phe Thr Leu Arg Asn Thr Lys Ile Lys Lys
    1865                1870                1875
```

-continued

| | | | | | | | | | |
|---|---|---|---|---|---|---|---|---|---|
| Gly | Ser | Gln | Lys | Gly | Arg | Pro | Ser | Gly | Arg | Val | Val | Thr | Gln | Tyr |

Gly Ser Gln Lys Gly Arg Pro Ser Gly Arg Val Val Thr Gln Tyr
1880            1885              1890

His Tyr Thr Gln Trp Pro Asp Met Gly Val Pro Glu Tyr Ser Leu
1895            1900              1905

Pro Val Leu Thr Phe Val Arg Lys Ala Ala Tyr Ala Lys Arg His
1910            1915              1920

Ala Val Gly Pro Val Val His Cys Ser Ala Gly Val Gly Arg
1925            1930              1935

Thr Gly Thr Tyr Ile Val Leu Asp Ser Met Leu Gln Gln Ile Gln
1940            1945              1950

His Glu Gly Thr Val Asn Ile Phe Gly Phe Leu Lys His Ile Arg
1955            1960              1965

Ser Gln Arg Asn Tyr Leu Val Gln Thr Glu Glu Gln Tyr Val Phe
1970            1975              1980

Ile His Asp Thr Leu Val Glu Ala Ile Leu Ser Lys Glu Thr Glu
1985            1990              1995

Val Leu Asp Ser His Ile His Ala Tyr Val Asn Ala Leu Leu Ile
2000            2005              2010

Pro Gly Pro Ala Gly Lys Thr Lys Leu Glu Lys Gln Phe Gln Leu
2015            2020              2025

Leu Ser Gln Ser Asn Ile Gln Gln Ser Asp Tyr Ser Ala Ala Leu
2030            2035              2040

Lys Gln Cys Asn Arg Glu Lys Asn Arg Thr Ser Ser Ile Ile Pro
2045            2050              2055

Val Glu Arg Ser Arg Val Gly Ile Ser Ser Leu Ser Gly Glu Gly
2060            2065              2070

Thr Asp Tyr Ile Asn Ala Ser Tyr Ile Met Gly Tyr Tyr Gln Ser
2075            2080              2085

Asn Glu Phe Ile Ile Thr Gln His Pro Leu Leu His Thr Ile Lys
2090            2095              2100

Asp Phe Trp Arg Met Ile Trp Asp His Asn Ala Gln Leu Val Val
2105            2110              2115

Met Ile Pro Asp Gly Gln Asn Met Ala Glu Asp Glu Phe Val Tyr
2120            2125              2130

Trp Pro Asn Lys Asp Glu Pro Ile Asn Cys Glu Ser Phe Lys Val
2135            2140              2145

Thr Leu Met Ala Glu Glu His Lys Cys Leu Ser Asn Glu Glu Lys
2150            2155              2160

Leu Ile Ile Gln Asp Phe Ile Leu Glu Ala Thr Gln Asp Asp Tyr
2165            2170              2175

Val Leu Glu Val Arg His Phe Gln Cys Pro Lys Trp Pro Asn Pro
2180            2185              2190

Asp Ser Pro Ile Ser Lys Thr Phe Glu Leu Ile Ser Val Ile Lys
2195            2200              2205

Glu Glu Ala Ala Asn Arg Asp Gly Pro Met Ile Val His Asp Glu
2210            2215              2220

His Gly Gly Val Thr Ala Gly Thr Phe Cys Ala Leu Thr Thr Leu
2225            2230              2235

Met His Gln Leu Glu Lys Glu Asn Ser Val Asp Val Tyr Gln Val
2240            2245              2250

Ala Lys Met Ile Asn Leu Met Arg Pro Gly Val Phe Ala Asp Ile
2255            2260              2265

Glu Gln Tyr Gln Phe Leu Tyr Lys Val Ile Leu Ser Leu Val Ser

-continued

```
              2270                2275                2280
Thr  Arg  Gln  Glu  Glu  Asn  Pro  Ser  Thr  Ser  Leu  Asp  Ser  Asn  Gly
         2285                     2290                    2295

Ala  Ala  Leu  Pro  Asp  Gly  Asn  Ile  Ala  Glu  Ser  Leu  Glu  Ser  Leu
         2300                     2305                    2310
Val
```

USE OF PROTEIN TYROSINE PHOSPHATASE ZETA AS A BIOMOLECULAR TARGET IN THE TREATMENT AND VISUALIZATION OF BRAIN TUMORS

FIELD OF USE

The present invention relates to the use of proteins which are differentially expressed in primary brain tumor tissues, as compared to normal brain tissues, as biomolecular targets for brain tumor treatment therapies. Specifically, the present invention relates to the use of immunotherapeutic and immunoimaging agents which specifically bind to human protein tyrosine phosphatase-zeta (PTP$\zeta$) for the treatment and visualization of brain tumors in patients. The present invention also provides compounds and pharmaceutically acceptable compositions for administration in the methods of the invention.

BACKGROUND OF THE INVENTION
Brain Tumor Biology and Etiology

Brain tumors are considered to have one of the least favorable prognoses for long term survival: the average life expectancy of an individual diagnosed with a central nervous system (CNS) tumor is just eight to twelve months. Several unique characteristics of both the brain and its particular types of neoplastic cells create daunting challenges for the complete treatment and management of brain tumors. Among these are 1) the physical characteristics of the intracranial space, 2) the relative biological isolation of the brain from the rest of the body, 3) the relatively essential and irreplaceable nature of the organ mass, and 4) the unique nature of brain tumor cells.

First and foremost, the intracranial space and physical layout of the brain create significant obstacles to treatment and recovery. The brain is made of, primarily, astrocytes (which make up the majority of the brain mass, and serve as a scaffold and support for the neurons), neurons (which carry the actual electrical impulses of the nervous system,) and a minor contingent of other cells such as insulating oligodendrocytes (which produce myelin). These cell types give rise to primary brain tumors (e.g., astrocytomas, neuroblastomas, glioblastomas, oligodendrogliomas, etc.) Although the World Health Organization has recently established standard guidelines, the nomenclature for brain tumors is somewhat imprecise, and the terms astrocytoma and glioblastoma are often used broadly. The brain is encased in the relatively rigid shell of the skull, and is cushioned by the cerebrospinal fluid, much like a fetus in the womb. Because of the relatively small volume of the skull cavity, minor changes in the volume of tissue in the brain can dramatically increase intracranial pressure, causing damage to the entire organ (i.e., "water on the brain"). Thus, even small tumors can have a profound and adverse affect on the brain's function. In contrast, tumors in the relatively distensible abdomen may reach several pounds in size before the patient experiences adverse symptoms. The cramped physical location of the cranium also makes surgery and treatment of the brain a difficult and delicate procedure. However, because of the dangers of increased intracranial pressure from the tumor, surgery is often the first strategy of attack in treating brain tumors.

In addition to its physical isolation, the brain is chemically and biologically isolated from the rest of the body by the so-called "Blood-Brain-Barrier" (or BBB). This physiological phenomenon arises because of the "tightness" of the epithelial cell junctions in the lining of the blood vessels in the brain. Although nutrients, which are actively transported across the cell lining, may reach the brain, other molecules from the bloodstream are excluded. This prevents toxins, viruses, and other potentially dangerous molecules from entering the brain cavity. However, it also prevents therapeutic molecules, including many chemotherapeutic agents that are useful in other types of tumors, from crossing into the brain. Thus, many therapies directed at the brain must be delivered directly into the brain cavity (e.g., by an Ommaya reservoir), or administered in elevated dosages to ensure the diffusion of an effective amount across the BBB.

With the difficulties of administering chemotherapies to the brain, radiotherapy approaches have also been attempted. However, the amount of radiation necessary to completely destroy potential tumor-producing cells also produce unacceptable losses of healthy brain tissue. The retention of patient cognitive function while eliminating the tumor mass is another challenge to brain tumor treatment. Neoplastic brain cells are often pervasive, and travel throughout the entire brain mass. Thus, it is impossible to define a true "tumor margin," unlike, for example, in lung or bladder cancers. Unlike reproductive (ovarian, uterine, testicular, prostate, etc.), breast, kidney, or lung cancers, the entire organ, or even significant portions, cannot be removed to prevent the growth of new tumors. In addition, brain tumors are very heterogeneous, with different cell doubling times, treatment resistances, and other biochemical idiosyncrasies between the various cell populations that make up the tumor. This pervasive and variable nature greatly adds to the difficulty of treating brain tumors while preserving the health and function of normal brain tissue.

Although current surgical methods offer considerably better post-operative life for patients, the current combination therapy methods (surgery, low-dosage radiation, and chemotherapy) have only improved the life expectancy of patients by one month, as compared to the methods of 30 years ago. Without effective agents to prevent the growth of brain tumor cells that are present outside the main tumor mass, the prognosis for these patients cannot be significantly improved. Although some immuno-affinity agents have been proposed and tested for the treatment of brain tumors, see, e.g., the tenascin-targeting agents described in U.S. Pat. No. 5,624,659, these agents have not proven sufficient for the treatment of brain tumors. Thus, therapeutic agents which are directed towards new molecular targets, and are capable of specifically targeting and killing brain tumor cells, are urgently needed for the treatment of brain tumors.

Protein Tyrosine Phosphatase Receptors: Generally, and PTP-Zeta ($\zeta$)

Vital cellular functions, such as cell proliferation and signal transduction, are regulated in part by the balance between the activities of protein kinases and protein phosphatases. These protein-modifying enzymes add or remove a phosphate group from serine, threonine, or tyrosine residues in specific proteins. Some tyrosine kinases (PTK's) and phosphatases (PTPase's) have been theorized to have a role in some types of oncogenesis, which is thought to result from an imbalance in their activities. There are two classes of PTPase molecules: low molecular weight proteins with a single conserved phosphatase domain such as T-cell protein-tyrosine phosphatase (PTPT; MIM 176887), and high molecular weight receptor-linked PTPases with two tandemly repeated and conserved phosphatase domains separated by 56 to 57 amino acids. Examples of this latter group of receptor proteins include: leukocyte-common antigen (PTPRC; MIM 151460) and leukocyte antigen related tyrosine phosphatase (PTPRF; MIM 179590).

Kaplan et al. cloned 3 human receptor PTP genes, including PTP-γ ("Cloning of three human tyrosine phosphatases reveals a multigene family of receptor-linked protein-tyrosine-phosphatases expressed in brain." *Proc. Nat. Acad. Sci.* 87: 7000–7004 (1990).) It was shown that one PTPG allele was lost in 3 of 5 renal carcinoma cell lines and in 5 of 10 lung carcinoma tumor samples tested. PTP-γ mRNA was expressed in kidney cell lines and lung cell lines but not in several hematopoietic cell lines tested. Thus, the PTP-γ gene appeared to have characteristics suggesting that it may be a tumor suppressor gene in renal and lung carcinoma. Barnea et al. ("Identification of a carbonic anhydrase-like domain in the extracellular region of RPTP-gamma defines a new subfamily of receptor tyrosine phosphatases." *Molec. Cell. Biol.* 13: 1497–1506 (1993)) cloned cDNAs for the human and mouse PTP-γ gene (designated PTP-γ by that group) from brain cDNA libraries, and analyzed their predicted polypeptide sequences. The human (1,445-amino acid) and mouse (1,442-amino acid) sequences share 95% identity at the amino acid level and predict a putative extracellular domain, a single transmembrane domain, and a cytoplasmic region with 2 tandem catalytic tyrosine phosphatase domains. The extracellular domain contains a stretch of 266 amino acids that are highly similar to the zinc-containing enzyme carbonic anhydrase (MIM 114800), suggesting that PTP-γ and PTPξ represent a subfamily of receptor tyrosine phosphatases. The gene for PTP-γ has 30 exons and is approximately 780 kb in size. It is much larger than the other receptor PTP genes, with the CD45 gene (MIM 151460) being around 100 kb and the others even smaller.

Another receptor-type tyrosine phosphatase, protein tyrosine phosphatase zeta (PTPξ) [also known as PTPRZ, HPTP-ZETA, HPTPZ, RPTP-BETA(β), or RPTPB] was isolated as a cDNA sequence by two groups in the early nineties. The complete cDNA sequence of the protein is provided in SEQ ID NO. 1, and the complete deduced amino acid sequence is provided in SEQ ID NO. 2. Splicing variants and features are indicated in the sequences. Levy et al. ("The cloning of a receptor-type protein tyrosine phosphatase expressed in the central nervous system" *J. Biol. Chem.* 268: 10573–10581, (1993)) isolated cDNA clones from a human infant brain step mRNA expression library, and deduced the complete amino acid sequence of a large receptor-type protein tyrosine phosphatase containing 2,307 amino acids.

Levy found that the protein, which they designated PTP-β (PTPξ), is a transmembrane protein with 2 cytoplasmic PTPase domains and a 1,616-amino acid extracellular domain. As in PTP-γ (MIM 176886), the 266 N-terminal residues of the extracellular domain are have a high degree of similarity to carbonic anhydrases (see MIM 114880). The human gene encoding PTPξ has been mapped to chromosome 7q31.3-q32 by chromosomal in situ hybridization (Ariyama et al., "Assignment of the human protein tyrosine phosphatase, receptor-type, zeta (PTPRZ) gene to chromosome band 7q31.3" *Cytogenet. Cell Genet.* 70: 52–54 (1995)). Northern blot analysis has shown that showed that PTP-zeta is expressed only in the human central nervous system. By in situ hybridization, Levy et al. (1993) localized the expression to different regions of the adult human brain, including the Purkinje cell layer of the cerebellum, the dentate gyrus, and the subependymal layer of the anterior horn of the lateral ventricle. Levy stated that this was the first mammalian tyrosine phosphatase whose expression is restricted to the nervous system. In addition, high levels of expression in the murine embryonic brain were said to suggest an important role in CNS development.

Gebbink et al. isolated a mouse cDNA of 5.7 kb, encoding a 'new' member of the family of receptor-like protein-tyrosine phosphatases, termed RPTP-μ ("Cloning, expression and chromosomal localization of a new putative receptor-like protein tyrosine phosphatase." *FEBS Lett.* 290: 123–130 (1991)). The cDNA predicted a protein of 1,432 amino acids (not including the signal peptide) with a calculated molecular mass of 161,636. In addition, they cloned the human homolog, which showed 98.7% amino acid identity to the mouse protein. The predicted mouse protein consisted of a 722-amino acid extracellular region, containing 13 potential N-glycosylation sites, a single transmembrane domain, and a 688-amino acid intracellular part containing two tandem repeats homologous to the catalytic domains of other tyrosine phosphatases. RNA blot analysis showed a single transcript that was most abundant in lung but present in much lower amounts in brain and heart as well. The human PTP-μ gene was assigned to 18pter-q11 by Southern analysis of human/rodent somatic cell hybrid clones.

PTP-ε cDNA was isolated by Krueger et al. (Structural diversity and evolution of human receptor-like protein tyrosine phosphatases. EMBO J. 9:3241–3252, 1990.1990). The 700-amino acid protein has a short extracellular domain and two tandemly repeated intracellular PTPase domains. High levels of PTP-ε transcription were noted in the mouse brain and testes. Both iso forms of PTP-ε—a transmembrane, receptor-type isoform and a shorter, cytoplasmic one—appear to arise from a single gene through the use of alternative promoters and 5-prime exons.

Thus, the PTP receptor family of proteins has been characterized as a fairly diverse family of membrane-bound receptors, and non-membrane bound isoforms, which share a common PTPase cytosol domain architecture. Although their expression in fetal and embryonic tissues has suggested a developmental biology role for the proteins, their full function in normal and disease state biology is still not fully understood.

SUMMARY OF THE INVENTION

The present invention provides novel methods and reagents for specifically targeting brain tumor neoplastic cells for both therapeutic and imaging purposes. Thus, in a first aspect, the present invention provides PTPξ affinity-based compounds and compositions useful in treating a brain tumor in a patient. The compositions and compounds of this aspect of the invention generally fall into two groups: PTPξ-binding conjugate compounds, which comprise a cytotoxic moiety (C), which inhibits the growth of tumor cells; and PTPξ-binding compound compositions in which the PTPξ binding moiety alters the normal function of PTPξ in the tumor cell, thus inhibiting cell growth.

In a first group of embodiments of this aspect of the invention, PTPξ-binding therapeutic conjugate compounds are provided. These compounds have the general formula α(P$_z$)C, wherein α(P$_z$) is one or more moieties which specifically binds to a human protein tyrosine phosphatase-zeta, and C is one or more cytotoxic moieties. In preferred embodiments α(P$_z$) is an antibody or an antibody fragment. In particularly preferred embodiments, α(P$_z$) is an antibody or an antibody fragment which elicits a reduced immune response when administered to a human patient. Preferred cytotoxic moieties for use in these embodiments of the invention include radioactive moieties, chemotoxic moieties, and toxin proteins. The invention also provides compositions comprising these PTPξ-binding therapeutic conjugate compounds in a pharmaceutically acceptable carrier.

In a second group of embodiments of this first aspect of the invention, PTPξ-binding therapeutic compounds are provided which alter the normal function of PTPξ in brain tumor cells and inhibit brain tumor cell growth. These PTPξ-binding therapeutic compounds have the general formula α(P$_z$), wherein α(P$_z$) is one or more moieties which specifically binds to a human protein tyrosine phosphatase-zeta, and wherein the binding of α(P$_z$) alters the function of protein tyrosine phosphatase-zeta. In preferred embodiments α(P$_z$) is an antibody or an antibody fragment. In particularly preferred embodiments, α(P$_z$) is an antibody or an antibody fragment which elicits a reduced immune response when administered to a human patient. It is preferred that the therapeutic compounds of this second group of embodiments of the first aspect of the invention be formulated into therapeutic compositions comprising the PTPξ-binding compound in a pharmaceutically acceptable carrier.

In a second aspect, the present invention provides methods for using these compounds and compositions to treat a brain tumor in a patient. The methods comprise administering an effective amount of a composition, comprising a PTPξ-binding compound from the first or second group of embodiments of the first aspect and a pharmaceutically acceptable carrier, to a patient in need thereof. Brain tumors treated in this fashion may be glioblastomas, astrocytomas, neuroblastomas, or any type of brain tumor. Administration of the therapeutic composition may be by any acceptable means. One preferred method for administration is by intrathecal administration, although intravascular administration is also preferred.

In a third aspect, the present invention provides PTPξ affinity-based compounds and compositions for the visualization of brain tumors in patients. These compounds have the general formula α(P$_z$)I, wherein α(P$_z$) is one or more moieties which specifically binds to a human protein tyrosine phosphatase-zeta, and I is one or more imaging moieties. In preferred embodiments α(P$_z$) is an antibody or an antibody fragment. In particularly preferred embodiments, α(P$_z$) is an antibody or an antibody fragment which elicits a reduced immune response when administered to a human patient. Preferred I moieties include radiographic moieties (useful in, e.g., x-ray, scintillation, or other radiation imaging methods,) positron-emitting moieties, magnetic spin contrast moieties, and optically visible moieties (such as visible particles, fluorescent dyes, and visible-spectrum dyes.) It is preferred that the imaging compounds of these embodiments of the third aspect of the invention be formulated into therapeutic compositions comprising the PTPξ-binding compound in a pharmaceutically acceptable carrier.

In a fourth aspect, the present invention provides methods of using the compounds and compositions of the third aspect of the invention to visualize a brain tumor in a patient. These methods generally comprise administering an effective amount of an imaging compound of the general formula α(P$_z$)I in a pharmaceutically acceptable carrier to the patient, and then visualizing the imaging moieties of the compound. Administration of the imaging composition may be by any acceptable means. Intravascular administration of the imaging composition is preferred in these methods, although intrathecal administration is also preferred. Preferred methods of visualizing the imaging moieties of the compounds include radiographic imaging techniques (e.g., x-ray imaging and scintillation imaging techniques), positron-emission tomography, magnetic resonance imaging techniques, and direct or indirect (e.g., endoscopic) visual inspection.

DETAILED DESCRIPTION OF THE INVENTION

Figure 1:
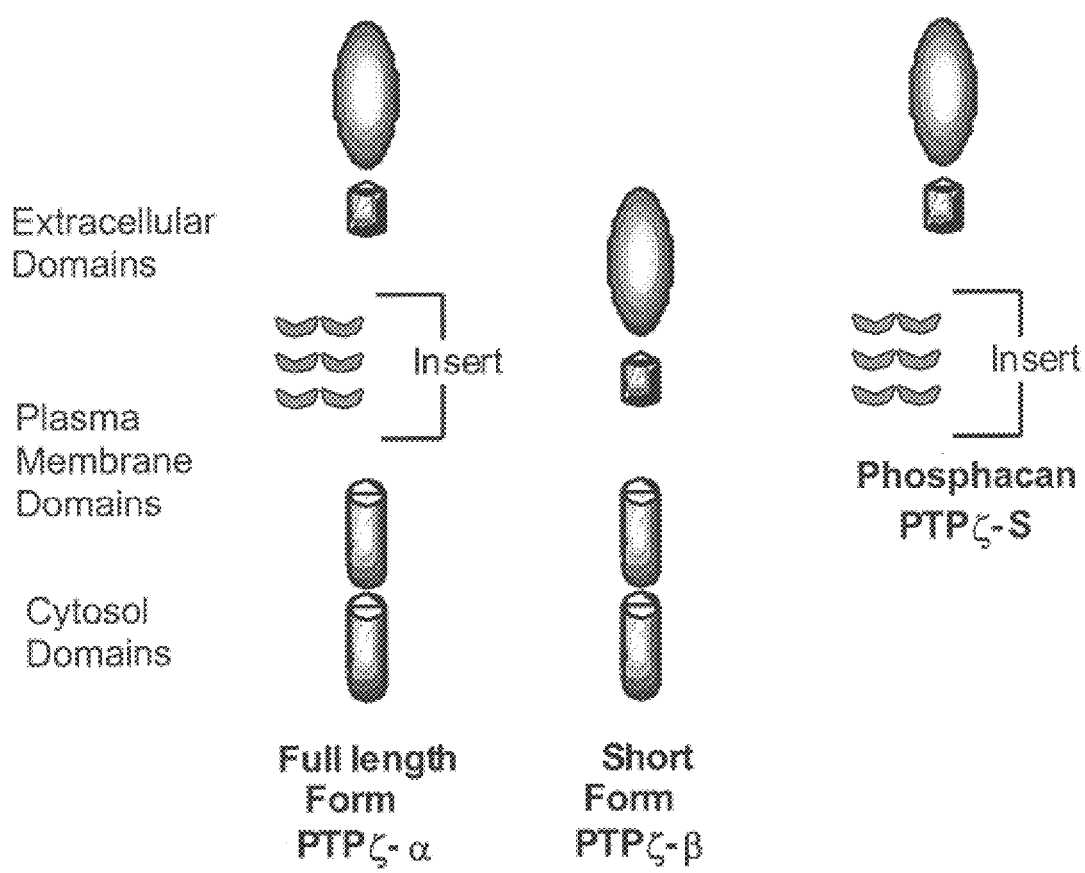
FIG. 1: A diagram of the three known splicing variant isoforms of PTPξ. The approximate position of the domains of the isoforms is indicated at the left. Isoform PTPξ-α is the full length isoform, which contains the primary amino acid sequence aa 25–2314 of SEQ ID NO. 2 (aa 1–24 are a signal polypeptide). In Isoform PTPξ-β, aa 755–1614 are missing. Isoform PTPξ-S (phosphacan), is a secreted isoforn which comprise the extracellular domains of PTPξ-α, in which the transmembrane and cytosol domains are missing.

Applicants have identified protein tyrosine phosphatase zeta (PTPξ) as a gene which is differentially regulated between brain cancer tissue (glioblastoma) and normal brain tissue. Applicants have performed differential cloning between cancerous and normal brains and have identified the PTPξ gene by DNA sequence analysis. Based on the observation in other diseases, particularly other cancers, in which overexpressed genes can contribute to the pathology of the disease, these overexpressed genes and their protein products are expected to mediate the initiation and progression of brain tumors. Thus, the overexpressed PTPξ protein, which is presented on the cell surface, provides an excellent target for immunotherapeutic agents which either deliver cytotoxic agents to directly promote tumor cell death, or which alter the function of PTPξ to inhibit the normal physiology of the tumor cell. In addition, immunoimaging agents targeted to PTPξ may be utilized to visualize the tumor mass either in diagnostic methods (e.g., magnetic resonance imaging (MRI) or radiography), or in surgery (e.g., by the use of optically visual dye moieties in the immunoimaging agent).

Applicants have identified PTPξ by a direct examination of the expression level of genes in actual tumor cells. These samples provide a more accurate and realistic picture of tumor cell biology, especially on the detailed transcriptome level, than animal models or established cell tissue culture cell lines. Several groups have found that cell lines established from astrocytomas and other cell lines do not exhibit expression patterns which reflect the actual expression of the original tumor. For instance, Schreiber, et. al., "Primary brain tumors differ in their expression of octamer deoxyribonucleic acid-binding transcription factors from long-term cultured glioma cell lines." *Neurosurgery* 34: 129–35 (1994), showed that nervous system-specific transcription factors known as N-Oct proteins are differentially expressed in human neuroblastoma and glioblastoma cell lines in vitro. However, when these results were compared to freshly isolated human primary and metastatic brain tumors, of the five astrocytomas and three glioblastomas analyzed, all but two tumors displayed the complete N-Oct protein profile, irrespective of histopathological tumor grade. Similarly, Eberle, et al., "The expression of angiogenin in tissue samples of different brain tumors and cultured glioma cells." *Anticancer Res* 20: 1679–84 (2000), could show that angiogenin is detectable in different kinds of intracranial tumor tissue samples. Although angiogenin could be detected in primary cultivated glioma cells, it was not detected in the permanent cell lines. Finally, Hartmann, et al., "The rate of homozygous CDKN2A/p16 deletions in glioma cell lines and in primary tumors." *Int J Oncol* 15: 975–82 (1999), showed that the rate of homozygous deletions of CDKN2A/p16 is variable between different tumor entities, but the rate of deletions is higher in established cell lines in comparison with primary tumors. Hartmann hypothesized that such incongruencies may reflect statistical sampling errors, true differences depending on tissue derivatization and CDKN2A/p16 loss under selective pressure in tissue culture. After comparing established cell lines derived from human glioblastomas and their corresponding primary tumors by multiplex PCR methodology, they found that in 2 of 11 cases (18%) the primary tumor had no p16 alteration whereas the corresponding cell lines had a homozygous p16 deletion, and that CDKN2A/p16 was lost already in the earliest passages of the cell lines. Thus, Hartmann concluded that the deletion was the result of selective cell-culture pressures in many cases.

These inconsistent results arise because the tumor tissue samples are obtained from their native milieu, without allowing them the opportunity to alter their gene expression levels in response to artificial environmental stimuli. As recently reported by the Brain Tumor Progress Review group of the National Cancer Institute in November, 2000, conventionally used glioblastoma cell lines contain genetic and gene expression alterations that are well defined and do not necessarily reflect the primary tumors from which they were derived. In addition, these cell lines are highly homogenous, unlike a primary brain tumor. Therefore, data derived soley from a cell line cannot reliably reflect the biology, heterogeneity, or therapeutic response of a primary brain tumor.

Applicants obtained tumor tissue, snap frozen in the operation hall from unknown patients, which was confirmed as glioblastoma grade IV by neuropathology. These tissues served as the experimental sample. Human whole brain tissue (Clontech Laboratories, Palo Alto, USA) served as control sample. Poly-A$^+$ RNA prepared from the cells was converted into double-stranded cDNA (dscDNA).

Briefly, the ds-cDNA's from control and disease states were subjected to kinetic re-annealing hybridization during which normalization of transcript abundances and enrichment for differentially expressed transcripts (i.e., subtraction) occurs. Normalized-subtracted ds-cDNAs were cloned into a plasmid vector, a large number of recombinant bacterial clones were picked, and their recombinant inserts were isolated by PCR. High-density cDNA arrays of those PCR products were screened with cDNA probes derived from the original control and disease states. Thus, only clones displaying a significant transcriptional induction and/or repression were sequenced and carried forward for massive expression profiling using a variety of temporal, spatial and disease-related probe sets.

The selected PCR products (fragments of 200–2000 bp in size) from clones showing a significant transcriptional induction and/or repression were sequenced and finctionally annotated in AGY's proprietary database structure (See WO01/13105). Because large sequence fragments were utilized in the sequencing step, the data generated has a much higher fidelity and specificity than other approaches, such as SAGE. The resulting sequence information was compared to public databases using the BLAST (blastn) and tblastx algorithm. PTPξ was identified as being expressed in glioblastoma cells at a level approximately 2.0 to 4.0 times the expression in normal brain cells. In the selected group from the subtractive library, 20 clones out of 20,000 were found to align with the PTPξ coding sequence.

Characteristics and Use of PTPξ

Thus, PTPξ was selected as a prime target for selective immuno-therapeutic agents in treating or imaging brain tumors. The complete cDNA sequence encoding PTPξ is provided in SEQ ID NO. 1, and the complete amino acid sequence encoding PTPξ is provided in SEQ ID NO. 2.

Three different splice variants have been described, which include two membrane bound variants (full length: PTPξ-α, and shorter version PTPξ-β) and one secreted form (Phosphacan). See FIG. 1. Isoform PTPξ-α is the full length isoform, which contains the primary amino acid sequence aa 25–2314 of SEQ ID NO. 2 (aa 1–24 are a signal polypeptide). In Isoform PTPξ-β, aa 755–1614 are missing. Isoform PTPξ-S (phosphacan), is a secreted isoform, which is comprises the extracellular domains of PTPξ-α. Northern Blot analysis have shown that the PTP zeta is exclusively expressed in the human central nervous system. In mouse embryos, the PTPξ transcript was mainly detected in the ventricular and subventricular zone of the brain and the spinal cord. The same pattern was detected in adult mice. Detailed studies have shown that during rat embryogenesis the two transmembrane splice variants of PTPξ are mainly expressed in glial precursor cells and that the secretory version (Phosphacan) is more abundant in mature astrocytes which have already migrated in the ventricle zone.

As used herein, a compound which specifically binds to human protein tyrosine phosphatase-zeta (PTPξ) is any compound (such as an antibody) which has a binding affinity for any naturally occurring isoform, spice variant, or polymorphism of PTPξ, explicitly including the three splice variants describe herein. As one of ordinary skill in the art will appreciate, such "specific" binding compounds (e.g., antibodies) may also bind to other closely related proteins which exhibit significant homology (such as greater than 90% identity, more preferably greater than 95% identity, and most preferably greater than 99% identity) with the amino acid sequence of PTPξ. Such proteins include truncated forms or domains of PTPξ, and recombinantly engineered alterations of PTPξ. For example, an portion of SEQ ID NO. 1 may be engineered to include a non-naturally occurring cysteine for cross-linking to an immunoconjugate protein, as described below.

In general, it is preferred that the antibodies utilized in the compositions and methods of the invention bind to the membrane-bound isoforms of the protein, as this will more specifically target the cytotoxic therapeutic agent, or the imaging agent, to the brain tumor cell. However, embodiments which utilize antibodies which bind to the secreted isoform of the protein are also useful in the invention, as one of ordinary skill would expect that the concentration of the secreted isoform would also be increased adjacent to brain tumor cells which over-express the protein.

The amino acid sequence of full length PTPξ consists of 2307 amino acids, as the sequence was deduced by Levy (in which aa 1722–1728 of SEQ ID NO. 2 were missing) (See also U.S. Pat. Nos. 5,604,094, and 6,160,090, fully incorporated herein by reference), or 2314 amino acids as the sequence was deduced by Krueger, et al., ("A human transmembrane protein-tyrosine phosphatase, PTP zeta, is expressed in brain and has an N-terminal receptor domain homologous to carbonic anhydrases" *Proc. nat. Acad. Sci. U.S.A.* 89:7417–7421 (1992)). Amino acids 1–24 of SEQ ID NO. 2 are a signal sequence which directs the proper placement of the transmembrane protein. The extracellular domain of the mature PTPξ protein spans amino acids 25–1635 of SEQ ID NO. 2 in the long and secreted forms (this forms the entire secreted form), and amino acids 25–754,1615–1635 in the short isoform. The transmembrane region of the protein spans amino acids 1636–1661 of SEQ ID NO. 2, and the balance of the protein forms the cytoplasmic domain, amino acids 1662–2314.

When raising antibodies to PTPξ, the entire protein (any of the three isoforms) or a portion thereof may be utilized.

For instance, the extracellular domain of the long or short form, the entire secreted form, or a portion of extracellular domain may be utilized. For instance, amino acids 25–754, which are common to both α and β isoforms, may be used. Such larger PTPξ proteins and domains may be produced utilizing any suitable recombinant vector/protein production system, such as the baculovirus transfection system outlined below, after being amplified from a fetal brain cDNA library (as available from, e.g., Clontech, Palo alto, Calif.) or another suitable genetic source. When utilizing an entire protein, or a larger section of the protein, antibodies may be raised by immunizing the production animal with the protein and a suitable adjuvant (e.g., Fruend's, Fruend's complete, oil-in-water emulsions, etc.). In these cases, the PTPξ protein (or a portion thereof) can serve as the PTPξ antigen. When a smaller peptide is utilized, it is advantageous to conjugate the peptide with a larger molecule to make an immunostimulatory conjugate for use as the PTPξ antigen. Commonly utilized conjugate proteins which are commercially available for such use include bovine serum albumin (BSA) and keyhole limpet hemocyanin (KLH). In order to raise antibodies to particular epitopes, peptides derived from the full PTPξ sequence may be utilized. Preferably, one or more 8–30 aa peptide portions of an extracellular domain of PTPξ are utilized, with peptides in the range of 10–20 being a more economical choice. Custom-synthesized peptides in this range are available from a multitude of vendors, and can be order conjugated to KLH or BSA. Alternatively, peptides in excess of 30 amino acids may be synthesized by solid-phase methods, or may be recombinantly produced in a suitable recombinant protein production system. In order to ensure proper protein glycosylation and processing, an animal cell system (e.g., Sf9 or other insect cells, CHO or other mammalian cells) is preferred. Other information useful in designing an antigen for the production of antibodies to PTPξ, including glycosylation sites, is provided in SEQ. ID NO. 2.

The extracellular domain of human PTPζ is known to bind to tenascin-C, tenascin-R, pleiotrophin (NM_002825), midkine (NM_002391), FGF-2 (XM_00366), Nr-CAM (NM_005010), L1/Ng-CAM, contactin (NM_001843), N-CAM (XM_006332), and axonin-INM_005076.) The first 5 of these molecules are either components of the extracellular matrix in gliomas or are soluble factors known to be present in gliomas, and the latter 4 are neuronal surface molecules. The binding of PTPξ to these molecules may play a significant role in the oncogenesis and growth of neoplastic cells in the brain. Thus, in alternative embodiments of the compositions and methods of the invention, antibody moieties are utilized which bind to PTPξ at a site on the protein which alters the binding of an extracellular ligand molecule to PTPξ. Such PTPξ activity altering antibodies may be utilized in therapeutic compositions in an unconjugated form (e.g., the antibody in an acceptable pharmaceutical carrier), or may be conjugated to either a therapeutic moiety (creating a double-acting therapeutic agent) or an imaging moiety (creating a duel therapeutic/imaging agent).

Selection of antibodies which alter (enhance or inhibit) the binding of a ligand to PTPξ may be accomplished by a straightforward binding inhibition/enhancement assay. According to standard techniques, the binding of a labeled (e.g., fluorescently or enzyme-labeled) antibody to PTPξ which has been immobilized in a microtiter well, is assayed in both the presence and absence of the ligand. The change in binding is indicative of either an enhancer (increased binding) or competitive inhibitor (decreased binding) relationship between the antibody and the ligand. Such assays may be carried out in high-throughput formats (e.g., 384 well plate formats, in robotic systems) for the automated selection of monoclonal antibody candidates for use as PTPξ ligand-binding inhibitors or enhancers.

In addition, antibodies which are useful for altering the function of PTPξ may be assayed in functional formats, such as glioblastoma cell culture or mouse/rat CNS tumor model studies. In glioblastoma cell models of activity, expression of PTPξ is first verified in the particular cell strain to be used. If necessary, the cell line may be stably transfected with a PTPξ coding sequence under the control of an appropriate constituent promoter, in order to express PTPξ at a level comparable to that found in primary tumors. The ability of the glioblastoma cells to survive in the presence of the candidate function-altering anti-PTPξ antibody is then determined. Similarly, In vivo models for human brain tumors, particularly nude mice/SCID mice model or rat models, have been described [Antunes, L., Angioi-Duprez, K. S., Bracard, S. R., Klein-Monhoven, N. A., Le Faou, A. E., Duprez, A. M., and Plenat, F. M. (2000). Analysis of tissue chimerism in nude mouse brain and abdominal xenograft models of human glioblastoma multiforme: what does it tell us about the models and about glioblastoma biology and therapy? *J Histochem Cytochem* 48, 847–58; Price, A., Shi, Q., Morris, D., Wilcox, M. E., Brasher, P. M., Rewcastle, N. B., Shalinsky, D., Zou, H., Appelt, K., Johnston, R. N., Yong, V. W., Edwards, D., and Forsyth, P. (1999). Marked inhibition of tumor growth in a malignant glioma tumor model by a novel synthetic matrix metalloproteinase inhibitor AG3340. *Clin Cancer Res* 5, 845–54; and Senner, V., Sturm, A., Hoess, N., Wassmann, H., and Paulus, W. (2000). In vivo glioma model enabling regulated gene expression. *Acta Neuropathol* (Berl) 99, 603–8.] Once correct expression of PTPξ in the tumor model is verified, the effect of the candidate anti-PTPξ antibodies on the tumor masses in these models can evaluated, wherein the ability of the anti-PTPξ antibody candidates to alter PTPξ activity is indicated by a decrease in tumor growth or a reduction in the tumor mass. Thus, antibodies which exhibit the appropriate anti-tumor effect may be selected without direct knowledge of a binding ligand.

Antibodies for Use in the Antibody-therapeutics Methods of the Invention

Generally, as the term is utilized in the specification, "antibody" or "antibody moiety" is intended to include any polypeptide chain-containing molecular structure that has a specific shape which fits to and recognizes an epitope, where one or more non-covalent binding interactions stabilize the complex between the molecular structure and the epitope. Antibodies which bind specifically to a human protein PTPξ are referred to as anti-PTPξ antibodies, or α($P_z$). The specific or selective fit of a given structure and its specific epitope is sometimes referred to as a "lock and key" fit. The archetypal antibody molecule is the immunoglobulin, and all types of immunoglobulins (IgG, IgM, IgA, IgE, IgD, etc.), from all sources (e.g., human, rodent, rabbit, cow, sheep, pig, dog, other mammal, chicken, turkey, emu, other avians, etc.) are considered to be "antibodies." Antibodies utilized in the present invention may be polyclonal antibodies, although monoclonal antibodies are preferred because they may be reproduced by cell culture or recombinantly, and may be modified to reduce their antigenicity.

Polyclonal antibodies may be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, an PTPξ antigen comprising an antigenic portion of the PTPξ polypeptide is initially injected into any of a wide variety of mammals (e.g., mice, rats, rabbits, sheep or goats). Alternatively, in order to generate antibodies to relatively short peptide portions of PTPξ (see discussion above), a superior immune response may be elicited if the polypeptide is joined to a carrier protein, such as ovalbumin, BSA or KLH. The peptide-conjugate is injected into the animal host, preferably according to a predetermined schedule incorporating one or more booster immnunizations, and the animals are bled periodically. Polyclonal antibodies specific for the polypeptide may then be purified from such antisera by, for example, affinity chromatography using the polypeptide coupled to a suitable solid support.

Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. The immortal cell line utilized is preferably selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

Preferably, the immortal fusion partners utilized are derived from a line that does not secrete immunoglobulin. The resulting fused cells, or hybridomas, are cultured under conditions that allow for the survival of fused, but not unfused, cells and the resulting colonies screened for the production of the desired monoclonal antibodies. Colonies producing such antibodies are cloned, expanded, and grown so as to produce large quantities of antibody, see Kohler and Milstein, 1975 Nature 256:495 (the disclosures of which are hereby incorporated by reference).

Large quantities of monoclonal antibodies from the secreting hybridomas may then be produced by injecting the clones into the peritoneal cavity of mice and harvesting the ascites fluid therefrom. The mice, preferably primed with pristine, or some other tumor-promoter, and immunosuppressed chemically or by irradiation, may be any of various suitable strains known to those in the art. The ascites fluid is harvested from the mice and the monoclonal antibody purified therefrom, for example, by CM Sepharose column or other chromatographic means. Alternatively, the hybridomas may be cultured in vitro or as suspension cultures. Batch, continuous culture, or other suitable culture processes may be utilized. Monoclonal antibodies are then recovered from the culture medium or supernatant.

Several monoclonal antibodies against PTPξ are currently available from commercial sources. For instance, BD Transduction Labs supplies a mouse anti-human MAB (WB, IH, IF), denominated "R20720", which recognizes the two transmembrane isoforms (PTPξ-α and PTPξ-β). Chemicon supplied a mouse anti-human MAB (WB, IH, IP), denominated "MAB5210", which recognizes both of the transmembrane isoforms, and also recognizes the soluble isoform (phosphacan, PTPξ-S). These antibodies are suitable for use in the compositions of the present invention, especially in Fab fragment form (which eliminates significant portions of the antigenic mouse constant heavy and light chain regions.) However, it is preferred that such antibodies by humanized or chimerized according to one of the procedures outlined below.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell.). When antibody gene synthesis is induced in the transfected host, the heavy and light chain proteins self-assemble to produce active antibodies that can be detected by screening with the antigen or immunogen.

Preferably, recombinant antibodies are produced in a recombinant protein production system which correctly glycosylates and processes the immunoglobulin chains, such as insect or mammalian cells. An advantage to using insect cells which utilize recombinant baculoviruses for the production of antibodies for use in the present invention is that the baculovirus system allows production of mutant antibodies much more rapidly than stably transfected mammalian cell lines. In addition, insect cells have been shown to correctly process and glycosylate eukaryotic proteins, which prokaryotic cells do not. Finally, the baculovirus expression of foreign protein has been shown to constitute as much as 50–75% of the total cellular protein late in viral infection, making this system an excellent means of producing milligram quantities of the recombinant antibodies.

The use of the baculovirus *Autographia californica* nuclear polyhedrosis virus (AcNPV) and recombinant viral stocks in *Spodoptera frugiperda* (Sf9) cells to prepare large quantities of protein has been described by Smith et al. (1985), Summers and Smith (1987). A preferred method of preparing recombinant antibodies is through the expression of DNA encoding recombinant antibody (produced by screening,. as above, or by protein engineering to include more human-like domains, as discussed below) via the baculoviral expression system in Sf9 insect cells. Production of recombinant proteins in Sf9 cells is well known in the art, and one of ordinary skill would be able to select from a number of acceptable protocols (e.g., that described in U.S. Pat. No. 6,603,905).

It should be noted that antibodies which have a reduced propensity to induce a violent or detrimental immune response in humans (such as anaphylactic shock), and which also exhibit a reduced propensity for priming an immune response which would prevent repeated dosage with the antibody therapeutic or imaging agent (e.g., the human-anti-murine-antibody "HAMA" response), are preferred for use in the invention. These antibodies are preferred for all administrative routes, including intrathecal administration. Even through the brain is relatively isolated in the cranial cavity, behind the blood brain barrier, an immune response still can occur in the form of increased leukocyte infiltration, and inflammation. Although some increased immune response against the tumor is desirable, the concurrent binding and inactivation of the therapeutic or imaging agent generally outweighs this benefit. Thus, humanized, chimeric, or xenogenic human antibodies, which produce less of an immune response when administered to humans, are preferred for use in the present invention.

Chimeric antibodies may be made by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference.) Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

Alternatively, polyclonal or monoclonal antibodies may be produced from animals which have been genetically altered to produce human immunoglobulins, such as the Abgenix XenoMouse or the Medarex HuMAb® technology. The transgenic animal may be produced by initially producing a "knock-out" animal which does not produce the animal's natural antibodies, and stably transforming the animal with a human antibody locus (e.g., by the use of a human artificial chromosome.) Only human antibodies are then made by the animal. Techniques for generating such animals, and deriving antibodies therefrom, are described in U.S. Pat. Nos. 6,162,963 and 6,150,584, incorporated fully herein by reference. Such fully human xenogenic antibodies are a preferred antibody for use in the methods and compositions of the present invention.

Alternatively, single chain antibodies (Fv, as described below) can be produced from phage libraries containing human variable regions. See U.S. Pat. No. 6,174,708, incorporated fully herein by reference. Also see Kuan, C. T., Reist, C. J., Foulon, C. F., Lorimer, I. A., Archer, G., Pegram, C. N., Pastan, I., Zalutsky, M. R., and Bigner, D. D. (1999). 125I-labeled anti-epidermal growth factor receptor-vIII single-chain Fv exhibits specific and high-level targeting of glioma xenografts. *Clin Cancer Res* 5, 1539–49;Lorimer, I. A., Keppler-Hafkemeyer, A., Beers, R. A., Pegram, C. N., Bigner, D. D., and Pastan, I. (1996). Recombinant immunotoxins specific for a mutant epidermal growth factor receptor: targeting with a single chain antibody variable domain isolated by phage display. *Proc Natl Acad Sci USA* 93, 14815–20; Pastan, I. H., Archer, G. E., McLendon, R. E., Friedman, H. S., Fuchs, H. E., Wang, Q. C., Pai, L. H., Herndon, J., and Bigner, D. D. (1995). Intrathecal administration of single-chain immunotoxin, LMB-7 [B3(Fv)-PE38], produces cures of carcinomatous meningitis in a rat model. *Proc Natl Acad Sci USA* 92, 2765–9, all of which are incorporated by reference fully herein.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Fv fragments are heterodimers of the variable heavy chain domain ($V_H$) and the variable light chain domain ($V_L$). The heterodimers of heavy and light chain domains that occur in whole IgG, for example, are connected by a disulfide bond. Recombinant Fvs in which $V_H$ and $V_L$ are connected by a peptide linker are typically stable, see, for example, Huston et al., Proc. Natl. Acad, Sci. USA 85:5879–5883 (1988) and Bird et al., Science 242:423–426 (1988), both fully incorporated herein, by reference. These are single chain Fvs which have been found to retain specificity and affinity and have been shown to be useful for imaging tumors and to make recombinant immunotoxins for tumor therapy. However, researchers have bound that some of the single chain Fvs have a reduced affinity for antigen and the peptide linker can interfere with binding. Improved Fv's have been also been made which comprise stabilizing disulfide bonds between the $V_H$ and $V_L$ regions, as described in U.S. Pat. No. 6,147,203, incorporated fully herein by reference. Any of these minimal antibodies may be utilized in the present invention, and those which are humanized to avoid HAMA reactions are preferred for use in embodiments of the invention.

In addition, derivatized immunoglobulins with added chemical linkers, detectable moieties [fluorescent dyes, enzymes, substrates, chemiluminescent moieties], or specific binding moieties [such as streptavidin, avidin, or biotin] may be utilized in the methods and compositions of the present invention. For convenience, the term "antibody" or "antibody moiety" will be used throughout to generally refer to molecules which specifically bind to an epitope of PTPξ, although the term will encompass all immunoglobulins, derivatives, fragments, recombinant or engineered immunoglobulins, and modified immunoglobulins, as described above.

Candidate anti-PTPξ antibodies can be tested for anti-PTPξ activity by any suitable standard means. As a first screen, the antibodies may be tested for binding against the PTPξ antigen utilized to produce them, or against the entire PTPξ extracellular domain or protein. As a second screen, anti-PTPξ candidates may be tested for binding to an appropriate glioblastoma cell line (i.e., one which approximates primary tumor PTPξ expression), or to primary tumor tissue samples. For these screens, the anti-PTPξ candidate antibody may be labeled for detection (e.g., with fluorescein or another fluorescent moiety, or with an enzyme such as horseradish peroxidase). After selective binding to PTPξ is established, the candidate antibody, or an antibody conjugate produced as described below, may be tested for appropriate activity (i.e., the ability to decrease tumor cell growth and/or to aid in visualizing tumor cells) in an in vivo model, such as an appropriate glioblastoma cell line, or in a mouse or rat human brain tumor model, as described above.

Therapeutic and Imaging Moieties, and Methods for Conjugating them with anti-PTPξ Antibodies to Use in the Compositions and Methods of the Invention As described above, the anti-PTPξ antibodies for use in the present invention may have utility on their own without conjugation, if they alter the native activity of PTPξ in the tumor cell. Such antibodies, which may be selected as described above, may be utilized without further modification to include a cytotoxic or imaging moiety. These types of compositions have the advantage of reduced toxicity (in that only the toxicity f the antibody moieties themselves must be taken into account when dosing), and are simpler to manufacture: thus, non-conjugated activity altering anti-PTPξ antibody therapeutics are a preferred embodiment of the invention. However, the conjugation of cytotoxic or imaging agents is yet another preferred embodiment when utilizing these antibodies, as the added moieties also add functionality to the therapeutic.

Thus, in many preferred embodiments of the invention, the anti-PTPξ antibodies may be coupled or conjugated to one or more therapeutic cytotoxic or imaging moieties. As used herein, "cytotoxic moiety" (C) simply means a moiety which inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. As utilized herein, "imaging moiety" (I) means a moiety which can be utilized to increase contrast between a tumor and the surrounded healthy tissue in a visualization technique (e.g., radiography, positron-emission tomography, magnetic resonance imaging, direct or indirect visual inspection.) Thus, suitable imaging moieties include radiography moieties (e.g. heavy metals and radiation emitting moieties), positron emitting moieties, magnetic resonance contrast moieties, and optically visible moieties (e.g., fluorescent or visible-spectrum dyes, visible particles, etc.). It will be appreciated by one of ordinary skill that some overlap exists between what is a therapeutic moiety and what is an imaging moiety. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques.

In general, therapeutic or imaging agents may be conjugated to the anti-PTPξ moiety by any suitable technique, with appropriate consideration of the need for pharmokinetic stability and reduced overall toxicity to the patient. A therapeutic agent may be coupled to a suitable antibody moiety either directly or indirectly (e.g. via a linker group). A direct reaction between an agent and an antibody is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance an antibody from an agent in order to avoid interference with binding capabilities. A linker group can also serve to increase the chemical reactivity of a substituent on a moiety or an antibody, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups may be designed into recombinant immunoglobulin molecules. It will be evident to those skilled in the art that a variety of bifunctional or polyfunctional reagents, both homo- and heterofunctional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the anti-PTPξ antibody moiety through a an oxidized carbohydrate group at a glycosylation site, as described in U.S. Pat. Nos. 5,057,313 and 5,156,840. Yet another alternative method of coupling the antibody moiety to the cytotoxic or imaging moiety is by the use of a non-covalent binding pair, such as streptavidin/biotin, or avidin/biotin. In these embodiments, one member of the pair is covalently coupled to the antibody moiety and the other member of the binding pair is covalently coupled to the cytotoxic or imaging moiety.

Where a cytotoxic moiety is more potent when free from the antibody portion of the immunoconjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one cytotoxic and/or imaging moiety to an antibody. By poly-derivatizing the anti-PTPξ antibody, several cytotoxic strategies may be simultaneously implemented, an antibody may be made useful as a contrasting agent for several visualization techniques, or a therapeutic antibody may be labeled for tracking by a visualization technique. In one embodiment, multiple molecules of an imaging or cytotoxic moiety are coupled to one antibody molecule. In another embodiment, more than one type of moiety may be coupled to one antibody. Regardless of the particular embodiment, immunoconjugates with more than one moiety may be prepared in a variety of ways. For example, more than one moiety may be coupled directly to an antibody molecule, or linkers which provide multiple sites for attachment (e.g., dendrimers) can be used. Alternatively, a carrier with the capacity to hold more than one cytotoxic or imaging moiety can be used.

A carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites, for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to anti-PTPξ antibody moieties for use in the invention, as a sufficient amount of the imaging moiety (dye, magnetic resonance contrast reagent, etc.) for detection may be more easily associated with the antibody moiety. In addition, encapsulation carriers are also useful in chemotoxic therapeutic embodiments, as they can allow the therapeutic compositions to gradually release a chemotoxic moiety over time while concentrating it in the vicinity of the tumor cells.

Carriers and linkers specific for radionuclide agents (both for use as cytotoxic moieties or positron-emission imaging moieties) include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionulcides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At may be conjugated to antibody moieties for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope may be utilized in the recited iodo-reagents. For example, a suitable antibody for use in the present invention may be easily made by coupling an Fab fragment of the BD Transduction Labs R20720 anti-PTPξ MAb with $^{131}$I Iodogen according to the manufacturer's instructions. Other radionuclides may be conjugated to anti-PTPξ antibody moieties by suitable chelation agents known to those of skill in the nuclear medicine arts.

Preferred chemotoxic agents include small-molecule drugs such as methotrexate, and pyrimidine and purine analogs. Preferred chemotoxin differentiation inducers include phorbol esters and butyric acid. Chemotoxic moieties may be directly conjugated to the anti-PTPξ antibody moiety via a chemical linker, or may encapsulated in a carrier, which is in turn coupled to the anti-PTPξ antibody moiety.

Preferred toxin proteins for use as cytotoxic moieties include ricin, abrin, diphtheria toxin, cholera toxin, gelonin, Pseudomonas exotoxin, Shigella toxin, pokeweed antiviral protein, and other toxin proteins known in the medicinal biochemistry arts. As these toxin agents may elicit undesirable immune responses in the patient, especially if injected intravascularly, it is preferred that they be encapsulated in a carrier for coupling to the anti-PTPξ antibody moiety.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions which may be utilized for x-ray radiography are described in U.S. Pat. No. 5,709,846, incorporated fully herein by reference. Such moieties may be conjugated to the anti-PTPξ antibody moiety through an acceptable chemical linker or chelation carrier. Positron emitting moieties for use in the present invention include $^{18}$F, which can be easily conjugated by a fluorination reaction with the anti-PTPξ antibody moiety according to the method described in U.S. Pat. No. 6,187,284.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the anti-PTPξ antibody moieties through a suitable chemical linker.

Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmacuetially acceptable dyes which have been approved for internal administration are preferred. In preferred embodiments, such dyes are encapsulated in carrier moieties, which are in turn conjugated to the anti-PTPξ antibody. Alternatively, visible particles, such as colloidal gold particles or latex particles, may be coupled to the anti-PTPξ antibody moiety via a suitable chemical linker.

Delivery of Therapeutic and Imaging Agents to the Patient The Blood Brain Barrier (BBB) and Administration Strategies At one time, the BBB was not considered to present a problem in the diagnosis and treatment of brain tumors, because early scans of human brain tumors suggested that the BTB (blood tumor barrier) was "leaky." This leakiness is relative, however: as the size of the molecule increases, the rate of movement across the barrier decreases. The BBB has been demonstrated to be heterogeneous in experimental human tumor xenograft animal models and in human patients. This lack of uniformity is because of the reduced integrity of tight junctions in the capillary endothelial cells of the tumor neovasculature, intratumoral variation in permeability, and altered intratumoral blood flow (Fuchs et al, 1990, *Cancer research* 50, 1954–59, Groothuis et al., 1984, *Prog.Exp. Tumor Res.*) Thus, although the BBB may not pose a delivery problem for some tumors in some patients, this cannot be said for all brain tumors across the board. In addition, a preferred mode of administration of the therapeutics of the invention is after removal of the main tumor mass (resection of the tumor), which destroys much of the "leaky" neovasculature. Moreover, as brain carcinomas are usually pervasive throughout the organ, therapies which are directed towards eradicating all tumor-producing cells cannot rely exclusively on the localized tumor neovasculature.

A first strategy for drug delivery through the BBB entails disruption of the BBB, either by osmotic means such as mannitol or leukotrienes, or biochemically by the use of vasoactive substances such as bradykinin. The potential for using BBB opening to target specific agents to brain tumors is also an option. In preferred embodiments, a BBB disrupting agent is co-administered with the therapeutic or imaging compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. However, the best current strategy for drug delivery behind the BBB is by intrathecal delivery of therapeutics or imaging agents directly to the cranium, as through an Ommaya reservoir.

Delivery/Administration of Therapeutic Antibodies

For administration, the antibody-therapeutic or antibody-imaging agent will generally be mixed, prior to administration, with a non-toxic, pharmaceutically acceptable carrier substance. Usually, this will be an aqueous solution, such as normal saline or phosphate-buffered saline (PBS), Ringer's solution, lactate-Ringer's solution, or any isotonic physiologically acceptable solution for administration by the chosen means. Preferably, the solution is sterile and pyrogen-free, and is manufactured and packaged under current Good Manufacturing Processes (GMP's), as approved by the FDA. The clinician of ordinary skill is familiar with appropriate ranges for pH, tonicity, and additives or preservatives when formulating pharmaceutical compositions for administration by intravascular injection, intrathecal injection, injection into the cerebro-spinal fluid, direct injection into the tumor, or by other routes. In addition to additives for adjusting pH or tonicity, the antibody-therapeutics and antibody-imaging agents may be stabilized against aggregation and polymerization with amino acids and non-ionic detergents, polysorbate, and polyethylene glycol. Optionally, additional stabilizers may include various physiologically-acceptable carbohydrates and salts. Also, polyvinylpyrrolidone may be added in addition to the amino acid. Suitable therapeutic immunoglobulin solutions which are stabilized for storage and administration to humans are described in U.S. Pat. No. 5,945,098, incorporated fully herein by reference. Other agents, such as human serum albumin (HSA), may be added to the therapeutic or imaging composition to stabilize the antibody conjugates.

The compositions of the invention may be administered using any medically appropriate procedure, e.g., intravascular (intravenous, intraarterial, intracapillary) administration, injection into the cerebrospinal fluid, intra-cavity or direct injection in the tumor. Intrathecal administration maybe carried out through the use of an Ommaya reservoir, in accordance with known techniques. (F.Balis et al., Am J. Pediatr. Hematol. Oncol. 11, 74, 76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

Intravascular injection may be by intravenous or intraarterial injection: carotid artery injection is thought to assist in administration to the brain, and is thus preferred. Antibody-agents injected into the blood stream have been shown to cross the blood-brain barrier and to infiltrate the cranial cavity to some extent, usually in the range of $10^{-4}$ to $10^{-3}\%$ injected dose per gram. This rate of uptake may be sufficient for imaging reagents, and also may be useful for tumor-cell specific cytotoxic agents (e.g, those specifically directed to the inhibition of the function of tumor-cell overexpressed proteins). However, in order to achieve therapeutic concentrations of the antibody-therapeutic agents without unacceptable toxicity to the patient, it is preferred that the therapeutics compositions be administered by intrathecal injection, direct injection, or injection into the cerebro-spinal fluid.

Thus, a preferred method for administration of the therapeutic compositions of the invention is by depositing it into the inner cavity of a cystic tumor by any suitable technique, such as by direct injection (aided by stereotaxic positioning of an injection syringe, if necessary) or by placing the tip of an Ommaya reservoir into a cavity, or cyst, for administration. Where the tumor is a solid tumor, the antibody may be administered by first creating a resection cavity in the location of the tumor. This procedure differs from an ordinary craniotomy and tumor resection only in a few minor respects. As tumor resection is a common treatment procedure, and is often indicated to relieve pressure, administration of the therapeutic compositions of the invention following tumor resection is a preferred embodiment of the treatment methods of the invention. Following gross total resection in a standard neurosurgical fashion, the cavity is preferable rinsed with saline until all bleeding is stopped by cauterization. Next the pia-arachnoid membrane, surrounding the tumor cavity at the surface, is cauterized to enhance the formation of fibroblastic reaction and scarring in the pia-arachnoid area. The result is the formation of an enclosed, fluid-filled cavity within the brain tissue at the location from where the tumor was removed. After the cyst has been formed, either the tip of an Ommaya reservoir or a micro catheter, which is connected to a pump device and allows the continuos infusion of an antibody solution into the cavity, can be placed into the cavity. See, e.g., U.S. Pat. No. 5,558,852, incorporated fully herein by reference.

Alternatively, a convention-enhanced delivery catheter may be implanted directly into the tumor mass, into a natural or surgically created cyst, or into the normal brain mass. Such convention-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 $\mu$l/minute), rather than diffusive flow, to deliver the therapeutic or imaging composition to the brain and/or tumor mass. Such devices are described in U.S. Pat. No. 5,720,720, incorporated fully herein by reference.

The effective amount of the therapeutic antibody-conjugate composition or of the imaging antibody-conjugate compositions to be given to a particular patient will depend on a variety of factors, several of which will be different from patient to patient. A competent clinician will be able to determine an effective amount of a therapeutic antibody-conjugate composition to administer to a patient to retard the growth and promote the death of tumor cells, or an effective amount of an imaging composition to administer to a patient to facilitate the visualization of a tumor. Dosage of the antibody-conjugate will depend on the treatment of the tumor, route of administration, the nature of the therapeutics, sensitivity of the tumor to the therapeutics, etc. Utilizing $LD_{50}$ animal data, and other information available for the conjugated cytotoxic or imaging moiety, a clinician can determine the maximum safe dose for an individual, depending on the route of administration. For instance, an intravenously administered dose may be more than an intrathecally administered dose, given the greater body of fluid into which the therapeutic composition is being administered.

Similarly, compositions which are rapidly cleared from the body may be administered at higher doses, or in repeated doses, in order to maintain a therapeutic concentration. As imaging moieties are typically less toxic than cytotoxic moieties, they may be administered in higher doses in some embodiments. Utilizing ordinary skill, the competent clinician will be able to optimize the dosage of a particular therapeutic or imaging composition in the course of routine clinical trials.

Typically the dosage will be 0.001 to 100 milligrams of conjugate per Kilogram subject body weight. Doses in the range of 0.01 to 1 mg per kilogram of patient body weight may be utilized for a radionuclide therapeutic composition which is administered intrathecally. Relatively large doses, in the range of 0.1 to 10 mg per kilogram of patient body weight, may used for imaging conjugates with a relatively non-toxic imaging moiety. The amount utilized will depend on the sensitivity of the imaging method, and the relative toxicity of the imaging moiety. In a therapeutic example, where the therapeutic composition comprises a $^{131}$I cytotoxic moiety, the dosage to the patient will typically start at a lower range of 10 mCi, and go up to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. Similarly, chemotoxic or toxin protein doses may be scaled accordingly.

The antibody conjugate can be administered to the subject in a series of more than one administration. For therapeutic compositions, regular periodic administration (e.g., every 2–3 days) will sometimes be required, or may be desirable to reduce toxicity. For therapeutic compositions which will be utilized in repeated-dose regimens, antibody moieties which do not provoke HAMA or other immune responses are preferred. The imaging antibody conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

The foregoing is intended to be illustrative of the embodiments of the present invention, and are not intended to limit the invention in any way. Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included herein. All publications and patent applications are herein incorporated by reference to the same extent as if each individual publication or patent application was specifically and individually indicated to be incorporated by reference.

We claim:

1. A method to treat a brain tumor comprising administering a therapeutic amount of a composition comprising:
a compound of the general formula $\alpha(P_\zeta)C$, wherein $\alpha(P_\zeta)$ specifically binds human protein tyrosine phosphatase-zeta, and C inhibits cell growth or promotes cell death;
and a pharmaceutically acceptable carrier.

2. The method of claim 1 wherein the therapeutic composition is administered by intrathecal administration.

3. The method of claim 1 wherein the therapeutic composition is administered by intravascular administration.

4. The method of claim 1 wherein the brain tumor is a glioblastoma.

5. The method of claim 1 wherein $\alpha(P_z)$ is selected from the group consisting of an antibody and an antibody fragment.

6. The method of claim 5 wherein $\alpha(P_\zeta)$ is an antibody selected from the group consisting of: monoclonal antibodies, polyclonal antibodies, humanized antibodies, recombinant antibodies, chemically modified antibodies, and synthetic antibodies.

7. The method of claim 5 wherein $\alpha(P_\zeta)$ is an antibody fragment selected from the group consisting of fragments of: monoclonal antibodies, polyclonal antibodies, humanized antibodies, recombinant antibodies, chemically modified antibodies, and synthetic antibodies.

8. The method of claim 1 wherein C is radioactive.

9. The method of claim 8 wherein C comprises a pharmaceutically acceptable radioactive isotope selected from the group consisting of $^{123}I$, $^{125}I$, $^{131}I$, $^{90}Y$, $^{211}At$, $^{67}Cu$, $^{186}Re$, $^{188}Re$, $^{212}Pb$, and $^{212}Bi$.

10. The method of claim 8 wherein C comprises a pharmaceutically acceptable radioactive isotope selected from the group consisting of $^{123}I$, $^{125}I$, $^{131}I$, and $^{211}At$.

11. The method of claim 1 wherein C is chemotoxic.

12. The method of claim 11 wherein C is selected from the group consisting of methotrexate, a pyrimidine, a purine, a phorbol ester, and butyric acid.

13. The method of claim 1 wherein C is a toxin protein.

14. The method of claim 13 wherein the toxin protein is selected from the group consisting of ricin, abrin, diphtheria toxin, cholera toxin, gelonin, Pseudomonas exotoxin, Shigella toxin, and pokeweed antiviral protein.

15. A compound for the treatment of a brain tumor of the general formula $\alpha(P_\zeta)C$, wherein $\alpha(P_\zeta)$ specifically binds human protein tyrosine phosphatasezeta, and C inhibits cell growth or promotes cell death.

16. The compound of claim 15 wherein $\alpha(P_z)$ is selected from the group consisting of an antibody and an antibody fragment.

17. The compound of claim 16 wherein $\alpha(P_\zeta)$ is an antibody selected from the group consisting of: monoclonal antibodies, polyclonal antibodies, humanized antibodies, recombinant antibodies, chemically modified antibodies, and synthetic antibodies.

18. The compound of claim 16 wherein $\alpha(P_\zeta)$ is an antibody fragment selected from the group consisting of fragments of: monoclonal antibodies, polyclonal antibodies, humanized antibodies, recombinant antibodies, chemically modified antibodies, and synthetic antibodies.

19. The compound of claim 15 wherein C is radioactive.

20. The compound of claim 15 wherein C comprises a pharmaceutically acceptable radioactive isotope selected from the group consisting of $^{123}I$, $^{125}I$, $^{131}I$, $^{90}Y$, $^{211}At$, $^{67}Cu$, $^{186}Re$, $^{188}Re$, $^{212}Pb$, and $^{212}Bi$.

21. The compound of claim 15 wherein C comprises a pharmaceutically acceptable radioactive isotope selected from the group consisting of $^{123}I$, $^{125}I$, and $^{131}I$.

22. The compound of claim 15 wherein C is chemotoxic.

23. The compound of claim 22 wherein C is selected from the group consisting of methotrexate, a pyrimidine, a purine, a phorbol ester, and butyric acid.

24. The compound of claim 15 wherein C is a toxin protein.

25. The compound of claim 24 wherein the toxin protein is selected from the group consisting of ricin, abrin, diphtheria toxin, cholera toxin, gelonin, Pseudomonas exotoxin, Shigella toxin, and pokeweed antiviral protein.

26. A method to treating a brain tumor comprising administering a therapeutic amount of a composition comprising:
a compound of the general formula $\alpha(P_\zeta)$, wherein $\alpha(P_\zeta)$ specifically binds human protein tyrosine phosphatase-zeta, and wherein binding of said $\alpha(P_\zeta)$ alters the binding of a ligand to said protein tyrosine phosphatase-zeta,
and a pharmaceutically acceptable carrier.

27. The method of claim 26 wherein the therapeutic composition is administered by intrathecal administration.

28. The method of claim 26 wherein the therapeutic composition is administered by intravascular administration.

29. The method of claim 26 wherein the brain tumor is a glioblastoma.

30. The method of claim 26 wherein $\alpha(P_z)$ is selected from the group consisting of an antibody and an antibody fragment.

31. The method of claim 30 wherein $\alpha(P_\zeta)$ is an antibody selected from the group consisting of: monoclonal antibodies, polyclonal antibodies, humanized antibodies, recombinant antibodies, chemically modified antibodies, and synthetic antibodies.

32. The method of claim 30 wherein $\alpha(P_\zeta)$ is an antibody fragment selected from the group consisting of fragments of: monoclonal antibodies, polyclonal antibodies, humanized antibodies, recombinant antibodies, chemically modified antibodies, and synthetic antibodies.

33. A method for visualizing a brain tumor in a patient, the method comprising:
a) administering to a patient an effective amount of an imaging composition comprising: a compound of the general formula $\alpha(P_\zeta)I$, wherein $\alpha(P_\zeta)$ specifically binds human protein tyrosine phosphatase-zeta, and I increases contrast between a tumor and surrounding tissue in a visualization method; and a pharmaceutically acceptable carrier; and b) visualizing said imaging composition.

34. The method of claim 33 wherein the imaging composition is administered by intrathecal administration.

35. The method of claim 33 wherein the imaging composition is administered by intravascular administration.

36. The method of claim 33 wherein the brain tumor is a glioblastoma.

37. The method of claim 33 wherein $\alpha(P_z)$ is selected from the group consisting of an antibody and an antibody fragment.

38. The method of claim 37 wherein $\alpha(P_\zeta)$ is an antibody selected from the group consisting of: monoclonal antibodies, polyclonal antibodies, humanized antibodies, recombinant antibodies, chemically modified antibodies, and synthetic antibodies.

39. The method of claim 37 wherein $\alpha(P_\zeta)$ is an antibody fragment selected from the group consisting of fragments of: monoclonal antibodies, polyclonal antibodies, humanized antibodies, recombinant antibodies, chemically modified antibodies, and synthetic antibodies.

40. The method of claim 33 wherein I is a radiographic moiety.

41. The method of claim 40 wherein the radiographic moiety comprises iodine or an iodine isotope.

42. The method of claim 40 wherein the visualization in step (b) is by x-ray imaging.

43. The method of claim 40 wherein the visualization in step (b) is by scintillation imaging.

44. The method of claim 33 wherein I is a positron-emitting moiety.

45. The method of claim 44 wherein the positron-emitting moiety comprises $^{18}F$.

46. The method of claim 44 wherein the visualization in step (b) is by positron emission tomography.

47. The method of claim 33 wherein I is a magnetic spin contrast moiety.

48. The method of claim 47 wherein the magnetic spin contrast moiety comprises an ion selected from the group consisting of chromium(III), manganese(II), iron(II), nickel(II), copper(II), praseodymium(III), neodymium(III), samarium(III) and ytterbium(III).

49. The method of claim 47 wherein the visualization in step (b) is by magnetic resonance imaging.

50. The method of claim 33 wherein I is selected from the group consisting of an optically visible dye and an optically visible particle.

51. The method of claim 50 wherein the visualization method in step (b) is by direct visual inspection.

52. The method of claim 50 wherein the visualization method in step (b) is by visual inspection through an endoscopic instrument.

53. A composition for the visualization of a brain tumor comprising:
a compound of the general formula $\alpha(P_\zeta)I$, wherein $\alpha(P_\zeta)$ specifically binds human protein tyrosine phosphatase-zeta, and I increases contrast between a tumor and surrounding tissue in a visualization method; and
a pharmaceutically acceptable carrier.

54. The composition of claim 53 wherein $\alpha(P_z)$ is selected from the group consisting of an antibody and an antibody fragment.

55. The composition of claim 54 wherein $\alpha(P_\zeta)$ is an antibody selected from the group consisting of: monoclonal antibodies, polyclonal antibodies, humanized antibodies, recombinant antibodies, chemically modified antibodies, and synthetic antibodies.

56. The composition of claim 54 wherein $\alpha(P_\zeta)$ is an antibody fragment selected from the group consisting of fragments of: monoclonal antibodies, polyclonal antibodies, humanized antibodies, recombinant antibodies, chemically modified antibodies, and synthetic antibodies.

57. The composition of claim 53 wherein I is a radiographic moiety.

58. The composition of claim 57 wherein the radiographic moiety comprises iodine or an iodine isotope.

59. The composition of claim 53 wherein I is a magnetic-spin contrast moiety.

60. The composition of claim 59 wherein the magnetic spin contrast moiety comprises an ion selected from the group consisting of chromium(III), manganese(II), iron(II), nickel(II), copper(II), praseodymium(III), neodymium(III), samarium(III) and ytterbium(III).

61. The composition of claim 53 wherein I is a positron-emitting moiety.

62. The composition of claim 61 wherein the positron-emitting moiety comprises $^{18}F$.

63. The composition of claim 53 wherein I is selected from the group consisting of an optically visible dye and an optically visible particle.

* * * * *